United States Patent
Fessmann et al.

(10) Patent No.: US 7,300,469 B2
(45) Date of Patent: Nov. 27, 2007

(54) DIAMINOPYRAZOLE COMPOUNDS AND THE USE THEREOF IN THE OXIDATION DYEING OF KERATINOUS FIBRES

(75) Inventors: Thilo Fessmann, Aulnay Sous Bois (FR); Eric Terranova, Magagnose (FR)

(73) Assignee: L'Oreal, SA, Paris (FR)

( * ) Notice: Subject to any disclaimer, the term of this patent is extended or adjusted under 35 U.S.C. 154(b) by 0 days.

(21) Appl. No.: 10/468,303

(22) PCT Filed: Feb. 14, 2002

(86) PCT No.: PCT/FR02/00568

§ 371 (c)(1),
(2), (4) Date: Dec. 3, 2003

(87) PCT Pub. No.: WO02/070489

PCT Pub. Date: Sep. 12, 2002

(65) Prior Publication Data

US 2004/0143909 A1    Jul. 29, 2004

(30) Foreign Application Priority Data

Feb. 21, 2001 (FR) .................................. 01 02311

(51) Int. Cl.
*A61K 7/13* (2006.01)
(52) U.S. Cl. .................. 8/405; 8/406; 8/408; 8/410; 8/421; 8/570; 8/573; 8/649; 8/670; 548/300
(58) Field of Classification Search ............... 8/405, 8/406, 408, 409, 410, 421, 570, 573, 649, 8/659, 670; 548/300
See application file for complete search history.

(56) References Cited

U.S. PATENT DOCUMENTS

| | | | |
|---|---|---|---|
| 4,823,985 A | 4/1989 | Grollier et al. | 222/1 |
| 5,032,137 A | 7/1991 | Junino et al. | 8/410 |
| 5,061,289 A * | 10/1991 | Clausen et al. | 8/405 |
| 5,663,366 A * | 9/1997 | Neunhoeffer et al. | 548/371.4 |
| 5,718,731 A * | 2/1998 | Loewe et al. | 8/409 |

FOREIGN PATENT DOCUMENTS

| | | | |
|---|---|---|---|
| DE | 38 43 892 | | 6/1990 |
| DE | 42 34 885 | | 4/1994 |
| DE | 196 43 059 | * | 4/1998 |
| DE | 196 46 609 | | 5/1998 |
| FR | 2 586 913 | | 3/1987 |
| FR | 2 630 438 | | 10/1989 |

OTHER PUBLICATIONS

STIC Search Report dated Nov. 17, 2006.*
English language Derwent Abstract of DE 196 46 609, May 14, 1998.

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

The invention relates to novel diaminopyrazole having formula (I), wherein: $R_1$, $R_2$, identical or different, represent a $C_3$ $C_5$ mono- or polyhydroxyalkyl, isopropyl, n-propyl or ethyl group, said groups being linear or branched, and their physiologically acceptable salts. The invention also relates to a composition for dyeing keratinous fibres containing a compound having formula (I) and the method for using same.

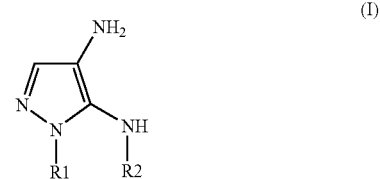

(I)

27 Claims, No Drawings

DIAMINOPYRAZOLE COMPOUNDS AND THE USE THEREOF IN THE OXIDATION DYEING OF KERATINOUS FIBRES

The present invention relates to novel diaminopyrazole derivatives, to a composition for the oxidation dyeing of keratin fibers, and in particular of human keratin fibers such as the hair, comprising at least one diaminopyrazole derivative as oxidation base, and to the oxidation dyeing processes using it.

It is known practice to dye keratin fibers, and in particular human hair, with dye compositions containing oxidation dye precursors, in particular ortho- or para-phenylenediamines, ortho-aminophenols or para-aminophenols and heterocyclic compounds such as diaminopyrazole derivatives, which are generally referred to as oxidation bases. The oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colors.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fiber, which may indeed be differently sensitized (i.e. damaged) between its tip and its root. They must also show good chemical stability in the formulations, and must have a good toxicological profile.

Furthermore, for a certain number of applications, dyes that produce chromatic shades on the hair are desired.

Patent application DE 42 34 885 discloses 4,5-diaminopyrazole derivatives, which, when used together with various couplers, especially benzoxazines, give chestnut-brown shades with blue, red, violet, aubergine or coppery glints.

However, these dyes do not satisfy all the above requirements.

The Applicant has now discovered, entirely surprisingly and unexpectedly, that it is possible to obtain dyes which are capable of producing powerful, particularly chromatic, bright and relatively unselective colorations, which have excellent properties of resistance to the various attacking factors to which keratin fibers may be subjected, by using as oxidation base the diaminopyrazoles of the formula (I) below or physiologically acceptable salts thereof.

One subject of the present invention is thus the novel diaminopyrazoles having the following general formula (I):

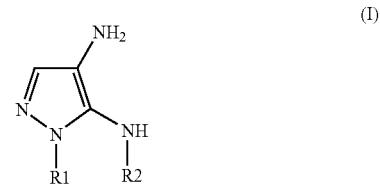

in which:

$R_1$ and $R_2$, which may be identical or different, denote a ethyl, n-propyl, isopropyl or mono- or polyhydroxy ($C_3$-$C_5$)alkyl group, it being possible for these groups to be linear or branched.

A subject of the invention is also the physiologically acceptable acid or base salts of the compounds of formula (I), such as the hydrochlorides, hydrobromides, sulfates, tartrates, lactates or acetates.

$R_1$ preferably denotes an ethyl, n-propyl, isopropyl, propyl, butyl or pentyl group which is substituted with one or more OH radicals, it being possible for these groups to be linear or branched.

$R_2$ preferably denotes a linear or branched ethyl, n-propyl, isopropyl, ethyl, propyl, butyl or pentyl group, which is substituted with one or more OH radicals.

A subject of the invention is also a composition for the oxidation dyeing of keratin fibers, and in particular of human keratin fibers such as the hair, characterized in that it contains, in a medium that is suitable for dyeing, as oxidation base, at least one diaminopyrazole of formula (I) above, or physiologically acceptable acid salts thereof.

As mentioned above, the colorations obtained with the oxidation dye composition in accordance with the invention are powerful, particularly bright and chromatic. They in particular produce shades that are free of or contain very little blue or yellow. Furthermore, they show excellent properties of resistance with respect to the action of various external agents (light, bad weather, washing, permanent-waving, perspiration and friction).

A subject of the invention is also a process for the oxidation dyeing of keratin fibers using such a dye composition.

As examples of diaminopyrazoles of formula (I) according to the invention, mention may be made of the following compounds:

| Structure | Name | Structure | Name | Structure | Name |
|---|---|---|---|---|---|
| ![structure] | 2,N3-diethyl-2H-pyrazole-3,4-diamine | ![structure] | N3-ethyl-2-propyl-2H-pyrazole-3,4-diamine | ![structure] | N3-ethyl-2-isopropyl-2H-pyrazole-3,4-diamine |
| ![structure] | 2-ethyl-N3-propyl-2H-pyrazole-3,4-diamine | ![structure] | 2,N3-dipropyl-2H-pyrazole-3,4-diamine | ![structure] | 2-isopropyl-N3-propyl-2H-pyrazole-3,4-diamine |
| ![structure] | 2-ethyl-N3-isopropyl-2H-pyrazole-3,4-diamine | ![structure] | N3-isopropyl-2-propyl-2H-pyrazole-3,4-diamine | ![structure] | 2,N3-diisopropyl-2H-pyrazole-3,4-diamine |
| ![structure] | 2-(4-amino-2-ethyl-2H-pyrazol-3-ylamino)-ethanol | ![structure] | 3-(4-amino-2-propyl-2H-pyrazol-3-ylamino)-propan-1-ol | ![structure] | 3-(4-amino-2-(3-hydroxypropyl)-2H-pyrazol-3-ylamino)-propan-1-ol |

| Structure | Name | Structure | Name | Structure | Name |
|---|---|---|---|---|---|
| (structure) | 3-(4-amino-5-ethyl-aminopyrazol-1-yl)-propan-1-ol | (structure) | 3-(4-amino-5-propyl-aminopyrazol-1-yl)-propan-1-ol | (structure) | 3-[4-amino-2-(2-hydroxypropyl)-2H-pyrazol-3-ylamino]-propan-1-ol |
| (structure) | 1-(4-amino-2-ethyl-2H-pyrazol-3-ylamino)-propan-2-ol | (structure) | 1-(4-amino-2-(2-hydroxypropyl)-2H-pyrazol-3-ylamino)-propan-2-ol | (structure) | 1-(4-amino-2-isobutyl-2H-pyrazol-3-ylamino)-propan-2-ol |
| (structure) | 1-(4-amino-5-ethyl-aminopyrazol-1-yl)propan-2-ol | (structure) | 4-[4-amino-2-(2-hydroxybutyl)-2H-pyrazol-3-ylamino]-butan-1-ol | (structure) | 4-(4-amino-2-isopropyl-2H-pyrazol-3-ylamino)-3-methyl-butan-1-ol |
| (structure) | 1-[4-amino-5-(2-hydroxyethylamino)pyrazol-1-yl]propan-2-ol | (structure) | 1-(4-amino-5-isopropylaminopyrazol-1-yl)propan-2-ol | (structure) | 3-(4-amino-5-ethylaminopyrazol-1-yl)propane-1,2-diol |

-continued

| Structure | Name | Structure | Name | Structure | Name |
|---|---|---|---|---|---|
| 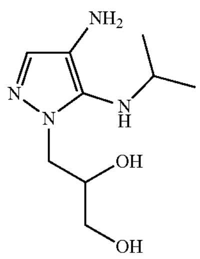 | 3-(4-amino-5-isopropylamino-pyrazol-1-yl)propane-1,2-diol | 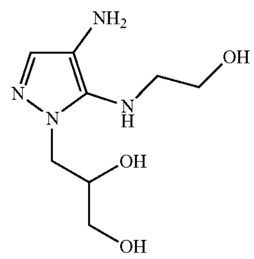 | 3-[4-amino-5-(2-hydroxyethyl-amino)-pyrazol-1-yl]propane-1,2-diol | 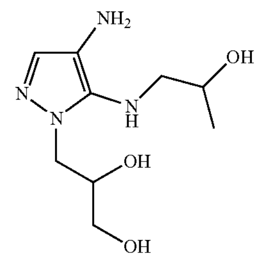 | 3-[4-amino-5-(2-hydroxypropylamino)-pyrazol-1-yl]propane-1,2-diol |
| 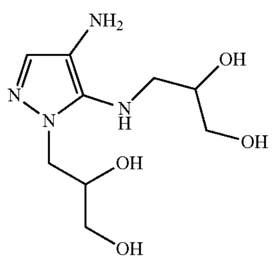 | 3-[4-amino-5-(2,3-dihydroxypropylamino)-pyrazol-1-yl]propane-1,2-diol | | | | |
| 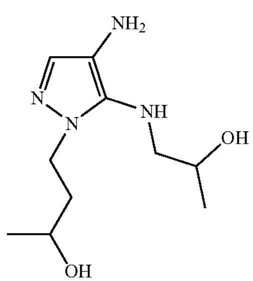 | 4-[4-amino-5-(2,3-dihydroxypropylamino)-pyrazol-1-yl]butane-2-ol | 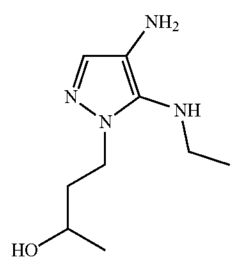 | 4-(4-amino-5-ethyl-amino-pyrazol-1-yl)butan-2-ol | 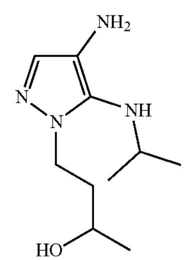 | 4-(4-amino-5-isopropylamino-pyrazol-1-yl)butan-2-ol |

-continued

| Structure | Name | Structure | Name | Structure | Name |
|---|---|---|---|---|---|
| | 4-(4-amino-2-ethyl-2H-pyrazol-3-ylamino)-butan-2-ol | | 4-(4-amino-2-ethyl-2H-pyrazol-3-ylamino)-butan-2-ol | | 4-(4-amino-2-propyl-2H-pyrazol-3-ylamino)-butan-2-ol | | 4-[4-amino-2-(3-hydroxybutyl)-2H-pyrazol-3-ylamino]-butan-2-ol |
| | 4-[4-amino-2-(3-hydroxybutyl)-2H-pyrazol-3-ylamino]-butan-2-ol | | 1-(4-amino-5-ethyl-aminopyrazol-1-yl)-butan-2-ol | | 1-(4-amino-5-ethyl-aminopyrazol-1-yl)-butan-2-ol | | 1-(4-amino-5-isopropylamino-pyrazol-1-yl)butan-2-ol |
| | 1-(4-amino-2-ethyl-2H-pyrazol-3-ylamino)-butan-2-ol | | 1-(4-amino-2-propyl-2H-pyrazol-3-ylamino)-butan-2-ol | | 1-[4-amino-2-propyl-2H-pyrazol-3-ylamino]-butan-2-ol | | 1-[4-amino-5-(2-hydroxybutyl-amino)-pyrazol-1-yl]butan-2-ol |
| | 1-(4-amino-5-ethyl-aminopyrazol-1-yl)-butan-2-ol | | 1-(4-amino-5-ethyl-aminopyrazol-1-yl)-butan-2-ol | | 4-[4-amino-5-(2-hydroxybutyl-amino)-pyrazol-1-yl]butane-1,2-diol | | 1-(4-amino-5-isopropylamino-pyrazol-1-yl)butan-2-ol |

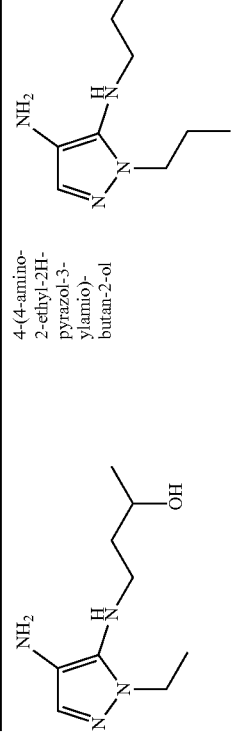
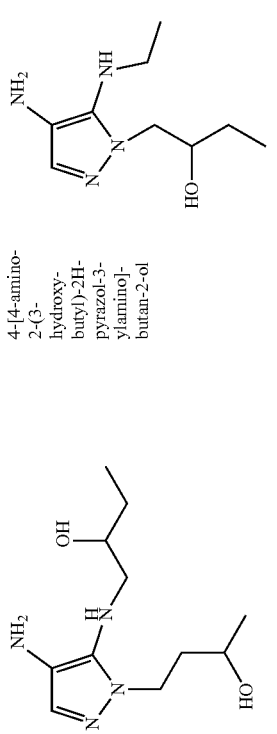
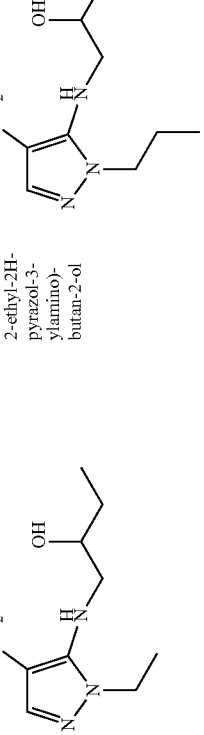
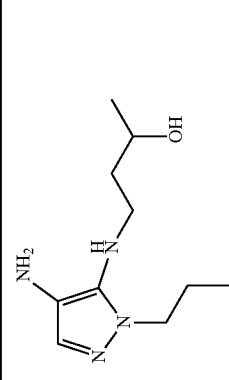
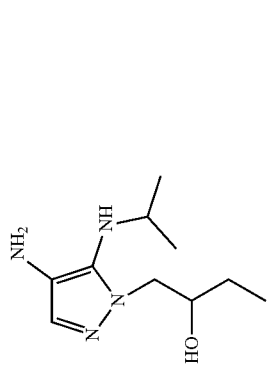
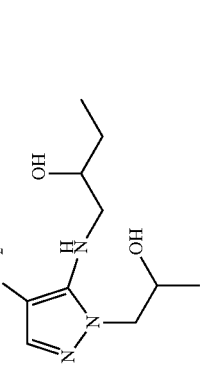
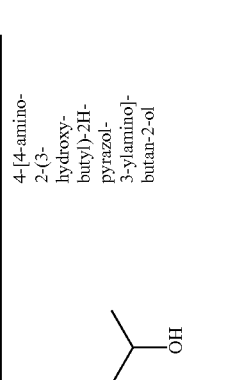
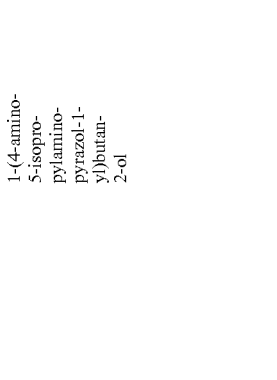
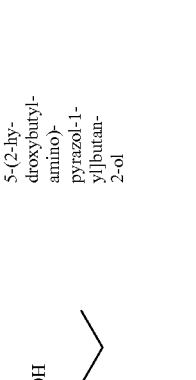
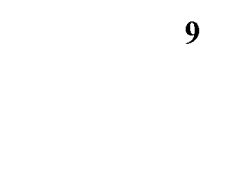
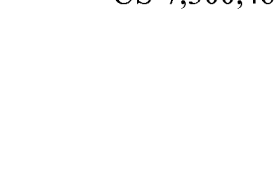

-continued

| Structure | Name | Structure | Name | Structure | Name |
|---|---|---|---|---|---|
| 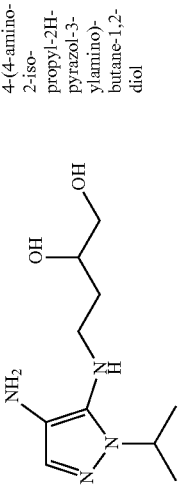 | 4-[4-amino-5-(3,4-di-hydroxybut-ylamino)-pyrazol-1-yl]butane-1,2-diol | 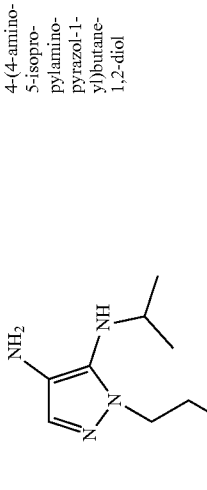 | 4-(4-amino-2-propyl-2H-pyrazol-3-ylamino)butane-1,2-diol | 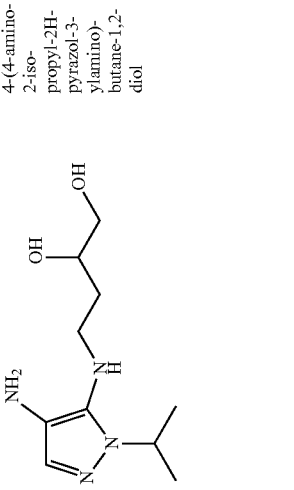 | 4-(4-amino-2-iso-propyl-2H-pyrazol-3-ylamino)butane-1,2-diol |
| 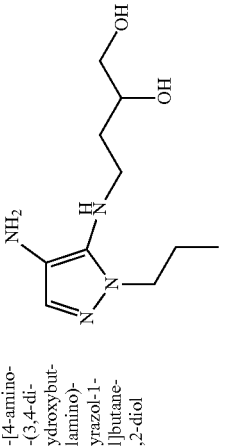 | 4-[4-amino-2-(3-hydroxybutyl)-2H-pyrazol-3-ylamino]butane-1,2-diol | 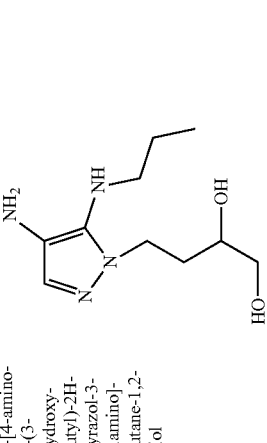 | 4-(4-amino-5-propyl-aminopyrazol-1-yl)butane-1,2-diol | 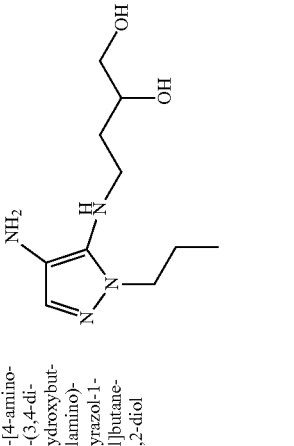 | 4-(4-amino-5-isopropylaminopyrazol-1-yl)butane-1,2-diol |
| 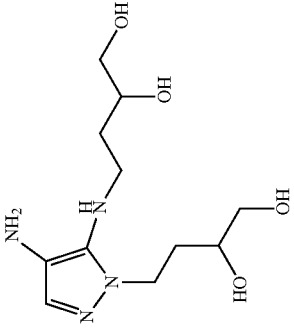 | 1-(4-amino-2-ethyl-2H-pyrazol-3-ylamino)butane-2,3-diol | 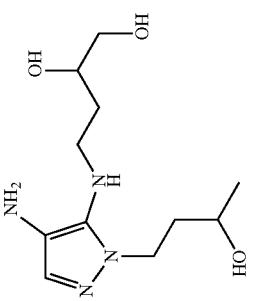 | 1-(4-amino-2-propyl-2H-pyrazol-3-ylamino)butane-2,3-diol | 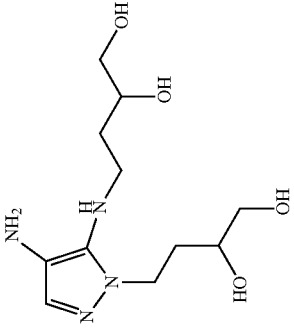 | 1-(4-amino-5-(2,3-dihydroxybutylamino)-pyrazol-1-yl)butane-2,3-diol |

-continued

| Structure | Name | Structure | Name | Structure | Name |
|---|---|---|---|---|---|
| (structure) | 1-(4-amino-5-ethyl-aminopyrazol-1-yl)-butane-2,3-diol | (structure) | 4-(4-amino-5-propyl-aminopyrazol-1-yl)-butane-1,2-diol | (structure) | 4-(4-amino-5-isopropylaminopyrazol-1-yl)butane-1,2-diol |
| (structure) | 4-(4-amino-2-ethyl-2H-pyrazol-3-ylamino)-butane-1,2,3-triol | (structure) | 4-[4-amino-5-(2,3,4-trihydroxybutyl)-aminopyrazol-1-yl]-butane-1,2,3-triol | (structure) | 4-(4-amino-2-isopropyl-2H-pyrazol-3-ylamino)-butane-1,2,3-triol |
| (structure) | 4-[4-amino-2-(3-hydroxy-2-methylpropyl)-2H-pyrazol-3-ylamino]-butane-1,2,3-triol | (structure) | 4-(4-amino-5-ethylaminopyrazol-1-yl)-butane-1,2,3-triol | (structure) | 4-(4-amino-5-isopropylaminopyrazol-1-yl)butane-1,2,3-triol |

-continued

| Structure | Name | Structure | Name | Structure | Name |
|---|---|---|---|---|---|
| (structure) | 3-[4-amino-2-(3-hydroxy-2-methylpropyl)-2H-pyrazol-3-ylamino]-2-methyl-propan-1-ol | (structure) | 2-[4-amino-5-(3-hydroxy-2-methylpropylamino)-pyrazol-1-ylmethyl]-propane-1,3-diol | (structure) | 3-[4-amino-2-(3-hydroxy-2-methylpropyl)-2H-pyrazol-3-ylamino]-2-methyl-propan-1-ol |
| (structure) | 3-(4-amino-5-ethyl-aminopyrazol-1-yl)-2-methyl-propan-1-ol | (structure) | 3-(4-amino-5-propylamino-pyrazol-1-yl)-2-methyl-propan-1-ol | (structure) | 3-(4-amino-5-iso-propylamino-pyrazol-1-yl)-2-methyl-propan-1-ol |
| (structure) | 2-[4-amino-5-(3-hydroxy-2,2-dimethyl-propylamino-pyrazol-1-ylmethyl]-propane-1,3-diol | (structure) | 3-(4-amino-2-propyl-2H-pyrazol-3-ylamino)-2,2-di-methyl-propan-1-ol | (structure) | 3-(4-amino-2-iso-propyl-2H-pyrazol-3-ylamino)-2,2-di-methyl-propan-1-ol |
| (structure) | 3-(4-amino-5-ethyl-aminopyrazol-1-yl)-2,2-di-methyl-propan-1-ol | (structure) | 3-[4-amino-5-(3-hydroxy-2,2-dimethyl-propyl)-amino(pyrazol-1-yl)]-2,2-di-methyl-propan-1-ol | (structure) | 3-(4-amino-5-isopropylamino-pyrazol-1-yl)-2,2-di-methyl-propan-1-ol |

-continued

| Structure | Name | Structure | Name | Structure | Name |
|---|---|---|---|---|---|
| (structure) | 3-(4-amino-2-ethyl-2H-pyrazol-3-ylamino)-2,2-dimethyl-propan-1-ol | (structure) | 2-[(4-amino-2-ethyl-2H-pyrazol-3-ylamino)methyl]-2,2-dimethylpropane-1,3-diol | (structure) | 2-[[4-amino-2-(3-hydroxy-2,2-dimethylpropyl)-2H-pyrazol-3-ylamino]methyl]-propane-1,3-diol |
| (structure) | 5-(4-amino-2-ethyl-2H-pyrazol-3-ylamino)pentan-1-ol | (structure) | 2-[(4-amino-2-propyl-2H-pyrazol-3-ylamino)methyl]-propane-1,3-diol | (structure) | 5-(4-amino-2-isopropyl-2H-pyrazol-3-ylamino)-pentan-1-ol |
| (structure) | 5-(4-amino-5-ethyl-aminopyrazol-1-yl)-pentan-1-ol | (structure) | 5-[(4-amino-2-(4-hydroxypentyl)-2H-pyrazol-3-ylamino]-pentan-1-ol | (structure) | 5-[4-amino-5-(5-hydroxypentylamino)-pyrazol-1-yl]pentan-1-ol |

-continued

| Structure | Name | Structure | Name | Structure | Name |
|---|---|---|---|---|---|
| | 1-(4-amino-2-ethyl-2H-pyrazol-3-ylamino)-3-methyl-butan-2-ol | | 1-[4-amino-5-(2-hydroxy-3-methylbutylamino)-pyrazol-1-yl]-3-methyl-butan-2-ol | | 1-(4-amino-2-isopropyl-2H-pyrazol-3-ylamino)-3-methyl-butan-2-ol |
| | 1-[4-amino-5-(2-hydroxy-3-methylbutylamino)-pyrazol-1-yl]-pentan-2-ol | | 1-(4-amino-5-ethyl-aminopyrazol-1-yl)-3-methyl-butan-2-ol | | 1-(4-amino-5-propyl-aminopyrazol-1-yl)-3-methyl-butan-2-ol |
| | 1-[4-amino-5-(2-hydroxypentyl-amino)-pyrazol-1-yl]pentan-2-ol | | 1-(4-amino-2-propyl-2H-pyrazol-3-ylamino)-pentan-2-ol | | 1-(4-amino-2-isopropyl-2H-pyrazol-3-ylamino)-pentan-2-ol |

-continued

| Structure | Name | Structure | Name | Structure | Name |
|---|---|---|---|---|---|
| 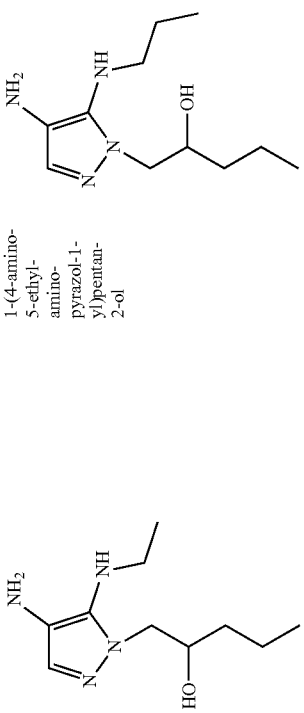 | 1-(4-amino-5-ethyl-amino-pyrazol-1-yl)pentan-2-ol | 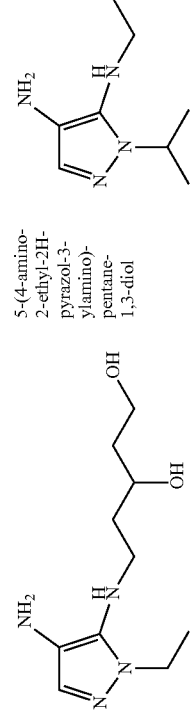 | 1-(4-amino-5-propyl-amino-pyrazol-1-yl)pentan-2-ol |  | 5-[4-amino-5-(3-hydroxypentylamino)-pyrazol-1-yl]-pentane-1,2-diol |
| 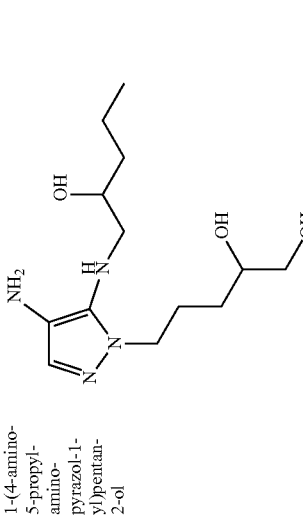 | 5-(4-amino-2-ethyl-2H-pyrazol-3-ylamino)pentane-1,3-diol | 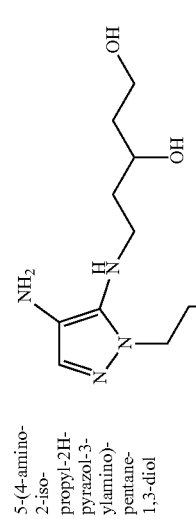 | 5-(4-amino-2-isopropyl-2H-pyrazol-3-ylamino)pentane-1,3-diol | 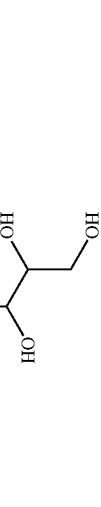 | 5-[4-amino-5-(3,5-dihydroxypentylamino)-pyrazol-1-yl]pentane-1,2,3-triol |
| 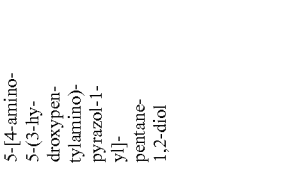 | 5-(4-amino-5-ethyl-aminopyrazol-1-yl)pentane-1,3-diol | 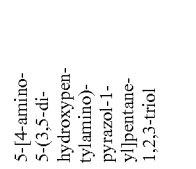 | 5-[4-amino-5-(3,5-dihydroxypentylamino)-pyrazol-1-yl]pentane-1,3-diol |  | 5-(4-amino-5-ethyl-aminopyrazol-1-yl)pentane-1,3-diol |

-continued

| Structure | Name | Structure | Name | Structure | Name |
|---|---|---|---|---|---|
| 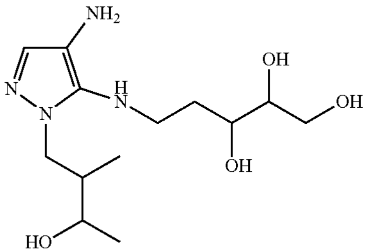 | 5-[4-amino-2-(3-hydroxy-2-methylbutyl)-2H-pyrazol-3-ylamino]-pentane-1,2,3-triol | 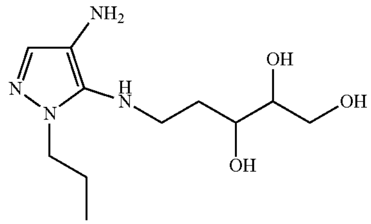 | 5-(4-amino-2-propyl-2H-pyrazol-3-ylamino)pentane-1,2,3-triol | 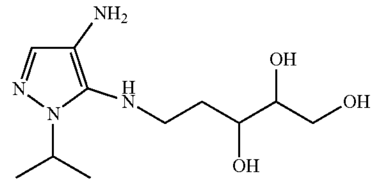 | 5-(4-amino-2-isopropyl-2H-pyrazol-3-ylamino)-pentane-1,2,3-triol |
| 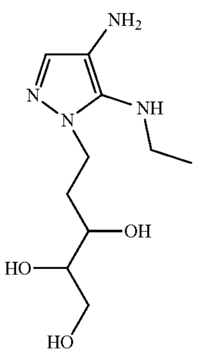 | 5-(4-amino-5-ethylamino-pyrazol-1-yl)pentane-1,2,3-triol | 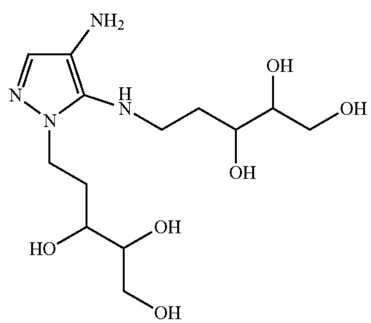 | 5-[4-amino-5-(3,4,5-trihydroxypentyl)amino)-pyrazol-1-yl]pentane-1,2,3-triol | 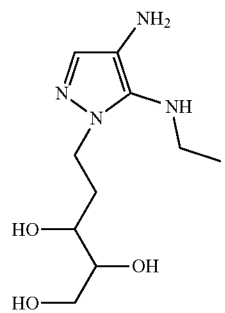 | 5-(4-amino-5-ethylamino-pyrazol-1-yl)pentane-1,2,3-triol |

| Structure | Name | Structure | Name | Structure | Name |
|---|---|---|---|---|---|
| (structure) | 5-(4-amino-2-ethyl-2H-pyrazol-3-ylamino)-pentane-1,2,3,4-tetraol | (structure) | 5-(4-amino-2-propyl-2H-pyrazol-3-ylamino)-pentane-1,2,3,4-tetraol | (structure) | 5-(4-amino-2-isopropyl-2H-pyrazol-3-ylamino)-pentane-1,2,3,4-tetraol |
| (structure) | 5-(4-amino-5-ethyl-amino-pyrazol-1-yl)pentane-1,2,3,4-tetraol | (structure) | 5-[4-amino-5-(2,3,4,5-tetrahydroxy-pentyl-amino)-pyrazol-1-yl]pentane-1,2,3,4-tetraol | (structure) | 5-[4-amino-2-(2-hydroxymethyl-butyl)-2H-pyrazol-3-ylamino]-pentane-1,2,3,4-tetraol |

Among the diaminopyrazoles of formula (I), preference is given to the following compounds:

| Structure | Name |
|---|---|
| 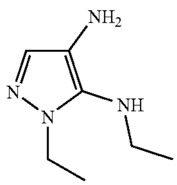 | 2,N3-diethyl-2H-pyrazole-3,4-diamine |
| 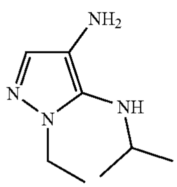 | 2-methyl-N3-isopropyl-2H-pyrazole-3,4-diamine |
| 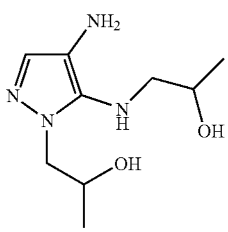 | 1-(4-amino-2-(2-hydroxypropyl)-2H-pyrazol-3-ylamino])-propan-2-ol |
| 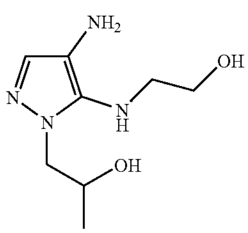 | 1-[4-amino-5-(2-hydroxyethylamino)pyrazol-1-yl]propan-2-ol |
| 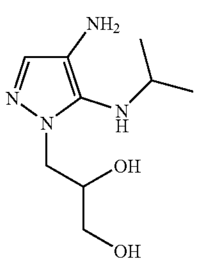 | 3-(4-amino-5-isopropylamino-pyrazol-1-yl)propane-1,2-diol |
| 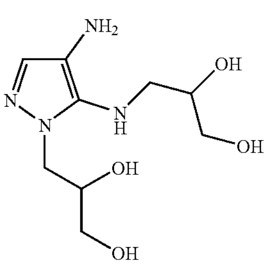 | 3-[4-amino-5-(2,3-dihydroxypropylamino)-pyrazol-1-yl]propane-1,2-diol |

-continued

| Structure | Name |
|---|---|
| 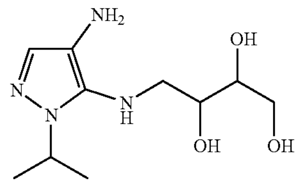 | 4-(4-amino-2-isopropyl-2H-pyrazol-3-ylamino)-butane-1,2,3-triol |
| 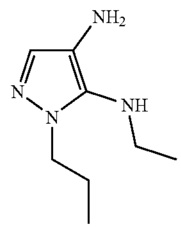 | N3-ethyl-2-propyl-2H-pyrazole-3,4-diamine |
| 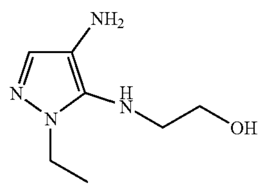 | 2-(4-amino-2-ethyl-2H-pyrazol-3-ylamino)-ethanol |
| 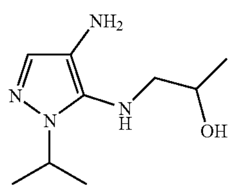 | 1-(4-amino-2-isobutyl-2H-pyrazol-3-ylamino)-propan-2-ol |
| 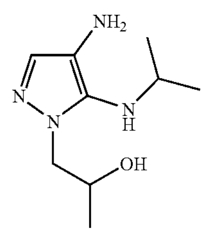 | 1-(4-amino-5-isopropylamino-pyrazol-1-yl)propan-2-ol |
| | 3-[4-amino-5-(2-hydroxyethylamino)-pyrazol-1-yl]-propane-1,2-diol |
| 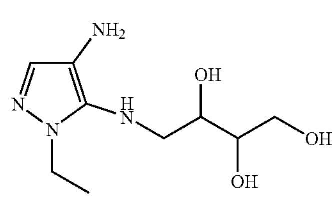 | 4-(4-amino-2-ethyl-2H-pyrazol-3-ylamino)-butane-1,2,3-triol |

| Structure | Name |
|---|---|
| 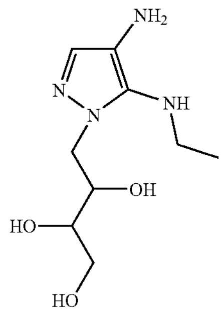 | 4-(4-amino-5-ethyl-aminopyrazol-1-yl)-butane-1,2,3-triol |
| | N3-ethyl-2-isopropyl-2H-pyrazole-3,4-diamine |
| 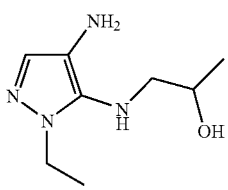 | 1-(4-amino-2-ethyl-2H-pyrazol-3-ylamino)-propan-2-ol |
| 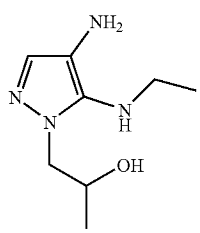 | 1-(4-amino-5-ethyl-amino-pyrazol-1-yl)propan-2-ol |
| 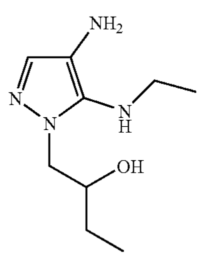 | 3-(4-amino-5-ethyl-amino-pyrazol-1-yl)propane-1,2-diol |
| 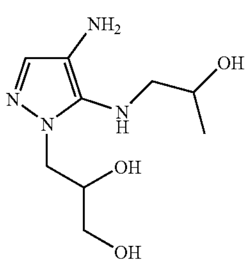 | 3-[4-amino-5-(2-hydroxypropylamino)-pyrazol-1-yl]propane-1,2-diol |
| | 4-[4-amino-5-(2,3,4-trihydroxy-butyl-amino)pyrazol-1-yl]-butane-1,2,3-triol |
| | 4-(4-amino-5-isopropylamino-pyrazol-1-yl)butane-1,2,3-triol |

The diaminopyrazoles of formula (I) that are more particularly preferred according to the invention are 2,N3-diethyl-2H-pyrazole-3,4-diamine
1-(4-amino-2-ethyl-2H-pyrazol-3-ylamino)propan-2-ol
N3-ethyl-2-isopropyl-2H-pyrazole-3,4-diamine
2-ethyl-N3-isopropyl-2H-pyrazole-3,4-diamine
2-(4-amino-2-ethyl-2H-pyrazol-3-ylamino)ethanol
1-(4-amino-2-ethyl-2H-pyrazol-3-ylamino)propan-2-ol
1-[4-amino-2-(2-hydroxypropyl)-2H-pyrazol-3-ylamino]propan-2-ol
1-(4-amino-5-ethylaminopyrazol-1-yl)propan-2-ol
3-(4-amino-5-ethylaminopyrazol-1-yl)propane-1,2-diol
or the addition physiologically acceptable acid salts thereof.

The diaminopyrazoles of formula (I) according to the invention are prepared, for example, according to the following general preparation method:

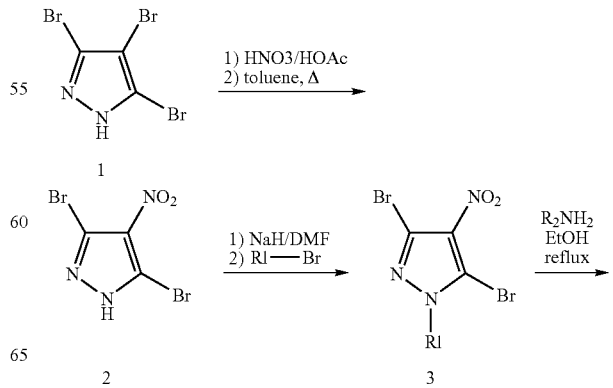

-continued

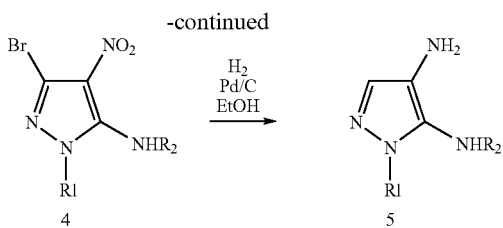

The synthetic approach shown below is described in the literature up to intermediate (2) (J. H. P. Juffermanns, C. L Habraken; J. Org. Chem., 1986, 51, 4656; Klebe et al., Synthesis, 1973, 294; R. Huttel, F. Buchele; Chem. Ber., 1955, 88, 1586). The alkylation and the amination to obtain the compounds of the type (5) of formula (I) according to the invention are mentioned, for example, in document DE 42 34 885.

The dye composition according to the invention especially contains from 0.001% to 10% by weight, preferably from 0.05% to 6% by weight and even more preferably from 0.1% to 3% by weight of at least one substituted N3-diaminopyrazole of formula (I) or salts thereof.

The dye composition in accordance with the invention may also contain, in addition to the diaminopyrazole(s) defined above, at least one additional oxidation base that may be chosen from the oxidation bases conventionally used in oxidation dyeing and among which mention may be made especially of para-phenylenediamines, bis(phenyl)alkylenediamines, para-aminophenols, ortho-aminophenols and heterocyclic bases other than the 4,5-diaminopyrazole used in accordance with the invention.

Among the para-phenylenediamines that may be mentioned more particularly, for example, are para-phenylenediamine, para-tolylenediamine, 2,6-dimethyl-para-phenylenediamine, 2-β-hydroxyethyl-para-phenylene-diamine, 2-n-propyl-para-phenylenediamine, 2-isopropyl-para-phenylenediamine, N-(62-hydroxypropyl)-para-phenylenediamine, N,N-bis(62-hydroxyethyl)-para-phenylenediamine, 4-amino-N-(62-methoxyethyl)aniline and the para-phenylenediamines described in French patent application FR 2 630 438, and the addition salts thereof.

Among the bis(phenyl)alkylenediamines that may be mentioned more particularly, for example, are N,N'-bis-(β-hydroxyethyl)-N,N'-bis(4'-aminophenyl)-1,3-diamino-propanol, N,N'-bis(β-hydroxyethyl)-N,N'-bis(4'-amino-phenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methyl-aminophenyl)tetramethylenediamine and N,N'-bis(ethyl)-N,N'-bis(4'-amino-3'-methylphenyl)ethylenediamine, and the addition salts thereof.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxy-ethylaminomethyl)phenol, and the addition salts thereof.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof.

Among the heterocyclic bases that may be mentioned more particularly, for example, are pyridine derivatives, pyrimidine derivatives, pyrazole derivatives other than the diaminopyrazoles of formula (I) used in accordance with the invention, and the addition salts thereof.

When they are used, these additional oxidation bases preferably represent from 0.0005% to 12% by weight relative to the total weight of the dye composition and even more preferably from 0.005% to 6% by weight relative this weight.

The oxidation dye compositions in accordance with the invention may also contain at least one coupler and/or at least one direct dye, especially to modify the shades or to enrich them with glints.

The couplers that may be used in the oxidation dye compositions in accordance with the invention may be chosen from the couplers conventionally used in oxidation dyeing, and among which mention may be made especially of meta-phenylenediamines, meta-amino-phenols, meta-diphenols, mono- or polyhydroxylated naphthalene derivatives and heterocyclic couplers such as, for example, indole or pyridine derivatives, and the addition salts thereof.

By way of examples, mention may be made of 2-methyl-5-aminophenol, 5-N-(β-hydroxyethyl)amino-2-methyl-phenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxy-ethyloxy)benzene, 2-amino-4-(β-hydroxyethylamino)-1-methoxybenzene, 1,3-diaminobenzene, 1,3-bis(2,4-di-aminophenoxy)propane, 3-ureidoaniline, 3-ureido-1-di-methylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxy-pyridine, 1-N-(β-hydroxyethyl)amino-3,4-methylene-dioxybenzene and 2,6-bis(β-hydroxyethylamino)toluene, and the addition salts thereof.

When they are present, these couplers especially represent from 0.0001% to 10% of the total weight of the dye composition, preferably from 0.005% to 5% by weight and even more preferably from 0.1% to 3% of this weight.

In general, the addition acid salts that may be used in the context of the dye compositions of the invention (oxidation bases and couplers) are chosen especially from the hydrochlorides, hydrobromides, sulfates, tartrates, lactates and acetates.

The medium that is suitable for dyeing (or support) used according to the invention consists of water or of a mixture of water and at least one organic solvent chosen from $C_1$-$C_4$ lower alkanols, polyols and polyol ethers, aromatic alcohols, similar products and mixtures thereof.

The dye composition according to the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, reducing agents, sunscreens, penetrating agents, sequestering agents, fragrances, buffers, dispersants, conditioners, for instance silicones, film-forming agents, preserving agents and opacifiers.

The pH of the dye composition according to the invention is between 3 and 12.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The dye composition according to the invention may be in various forms, such as in the form of liquids, creams or gels, or in any other form that is suitable for dyeing keratin fibers, and especially human hair.

Another subject of the invention is a process for dyeing keratin fibers, and in particular human keratin fibers such as the hair, using the dye composition as defined above.

According to this process, at least one dye composition as defined above is applied to the fibers, for a time that is sufficient to develop the desired coloration, either in air or using an oxidizing agent. The dye composition may optionally contain oxidation catalysts, so as to accelerate the oxidation process.

According to a first embodiment of the process of the invention, the coloration of the fibers may be performed without adding an oxidizing agent, solely by contact with atmospheric oxygen.

According to a second embodiment of the process of the invention, at least one dye composition as defined above is applied to the fibers, the color being revealed at acidic, neutral or alkaline pH using an oxidizing agent that is added to the composition just at the time of use, or which is present in an oxidizing composition applied simultaneously or sequentially in a separate manner.

According to this second embodiment of the dyeing process of the invention, the dye composition described above is preferably mixed, at the time of use, with an oxidizing composition containing, in a medium that is suitable for dyeing, at least one oxidizing agent present in an amount that is sufficient to develop a coloration. The mixture obtained is than applied to the keratin fibers and is left for an action time of 3 to 50 minutes and preferably 5 to 30 minutes, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulfates. Hydrogen peroxide is particularly preferred.

The pH of the oxidizing composition containing the oxidizing agent as defined above is such that, after mixing with the dye composition, the pH of the resulting composition applied to the keratin fibers preferably ranges between 3 and 12, and even more preferably between 5 and 11. It is adjusted to the desired value by means of acidifying or basifying agents usually used in the dyeing of keratin fibers, and as defined above.

The oxidizing composition as defined above may also contain various adjuvants conventionally used in compositions for dyeing the hair and as defined above.

The composition that is finally applied to the keratin fibers may be in various forms, such as in the form of liquids, creams or gels, or in any other form that is suitable for dyeing keratin fibers, and especially human hair.

Another subject of the invention is a multi-compartment device or dyeing "kit" or any other multi-compartment packaging system, a first compartment of which contains the dye composition as defined above, and a second compartment of which contains the oxidizing composition as defined above. These devices may be equipped with a means for applying the desired mixture to the hair, such as the devices described in patent FR-2 586 913 in the name of the Applicant.

The examples that follow are intended to illustrate the invention without, however, limiting its scope.

EXAMPLES

Examples of Synthesis

Synthesis of 3,4,5-tribromopyrazole (1)

An aqueous solution (350 ml) containing sodium hydroxide (24 g, 0.6 mol) and pyrazole (10 g, 0.147 mol) was prepared with stirring. After cooling the reaction medium to 20° C., $Br_2$ (72 g, 0.45 mol) was added dropwise over 1 hour, while maintaining the temperature between 20° C. and 25° C. The reaction was monitored by thin layer chromatography (TLC) (50% hexane/50% EtOAc or ethyl acetate). The precipitate was filtered off and washed with demineralized water (100 ml). The filtrate was acidified to pH 6-7 using HCl (10%, 33 g, 0.27 mol) and maintaining the temperature between 20 and 25° C. The precipitate thus formed was filtered off and washed with demineralized water (100 ml). The combined solids were maintained at reflux in Dean-Stark apparatus in the presence of toluene (200 ml). At the end of collection of the water, the organic phase was filtered while hot. The solvent was evaporated down to a residual volume of 110 ml. The solution was cooled to 0-5° C. for 1 hour. The precipitate formed was collected by filtration, washed with cold toluene (20 ml) and dried under vacuum at 80° C. to give the 3,4,5-tribromopyrazole (1) in the form of an off-white solid (30 g, 67%).

$^{13}$C-NMR: (100 MHz, $d_6$-DMSO): 97.7-116.1-126.4
Melting point: 182-184° C.

Synthesis of 3,5-dibromo-4-nitropyrazole (2)

$HNO_3$ (d=1.50 g/ml; 18 ml, 0.429 mol) was added dropwise over 10 minutes to a solution of 3,4,5-tribromopyrazole (1) (50 g, 0.164 mol) in glacial acetic acid (750 ml) while maintaining the temperature at 15° C. Acetic anhydride (250 ml) was added and the reaction mixture was stirred at room temperature for 2 hours. Once the reaction was complete, the reaction mixture was poured onto crushed ice (1 kg). After stirring for 1 hour, the crude product was filtered off and then washed with demineralized water (2×60 ml) to give crude 1-nitro-3,4,5-tribromopyrazole. The water (24.6 ml) contained in the wet product was removed by heating a solution of the product in toluene (750 ml) at reflux in Dean-Stark apparatus. The toluene solution was maintained at reflux for a further 30 minutes until a TLC (eluent: toluene) showed that the rearrangement of the 1-nitro-3,4,5-tribromopyrazole ($R_f$=0.77), the intermediate formed, into 3,5-dibromo-4-nitropyrazole 2 ($R_f$=0.05) was complete. The solution was concentrated to a residual volume of 150 ml and then cooled to 60° C., followed by addition of hexane (275 ml). The solution was cooled to 0-5° C. for 1 hour and the 3,5-dibromo-4-nitropyrazole (2) (29.1 g, 65%) was recovered by filtration and drying under vacuum in the form of a pale yellow solid.

Melting point: 127.6-130.1° C.

Synthesis of 3,5-dibromo-1-ethyl-4-nitro-1H-pyrazole (3)

A mixture of 4-nitro-3,5-dibromopyrazole (2) (20.0 g; 73.8 mmol) in DMF (160 ml) was added over 20 minutes to a suspension of NaH (3.3 g, 82.5 mmol; 60% dispersion in oil, prewashed with hexane) in DMF (160 ml) with stirring and under an inert atmosphere. After stirring for 30 minutes, a solution of bromoethane (19.3 g; 177.1 mmol) in DMF (35 ml) was added over 5 minutes. The reaction mixture was heated to 70° C. for 4 hours and the DMF was then evaporated off under reduced pressure (oil pump) while heating the reaction medium to 80° C. A DCM/water mixture (200 ml, 1/1) was added. The aqueous phase was washed with DCM (100 ml) and the combined organic phases were then washed with water (50 ml). The organic phase was dried over $NaSO_4$ and the solvent was evaporated off under reduced pressure. The crude 3,5-dibromo-1-ethyl-4-nitro-1H-pyrazole (19.6 g, 89%) is obtained in the form of a solid. This product is used without purification in the following step.

Synthesis of (5-bromo-2-ethyl-4-nitro-2H-pyrazol-3-yl)ethylamine (4-1)

A mixture of 3,5-dibromo-1-ethyl-4-nitro-1H-pyrazole (28.4 g; 95 mmol), EtOH (470 ml) and ethylamine (45.0 g, 700 mmol) was refluxed for 3 hours. The reaction medium was concentrated to the maximum under reduced pressure (rotary evaporator, water bath at 40° C.). The brown oil obtained was suspended in DCM (250 ml) and water (250 ml). The aqueous phase was washed with DCM (50 ml). The combined aqueous phases were extracted with DCM (50 ml) and the combined organic phases were then dried over $NaSO_4$. After evaporating off the solvent, a solid was obtained (24.6 g), which was purified by chromatography on silica gel (eluent: EtOAc/hexane) to give (5-bromo-2-ethyl-4-nitro-2H-pyrazol-3-yl)ethylamine (11.4 g, 45%) in the form of a yellow solid.

Melting point: 84.9-87.4° C. Elemental analysis ($C_7H_{11}N_4O_2Br$). Found: C, 31.92%; H, 4.05%; N, 21.14%; Br, 30.76%. Theory: C, 31.96%; H, 4.21%; N, 21.30%; Br, 30.37%. $^1$H-NMR (400 MHz, $CDCl_3$): 4.18 (2H, q, J=7.3 Hz, $NCH_2CH_3$); 3.53 (2H, qd, J=7.2 Hz and 5.9 Hz, $NHCH_2CH_3$), 1.46 (3H, t, J=7.3 Hz, $NCH_2CH_3$); 1,37 (3 h, t, J=7.2 Hz, $NHCH_2CH_3$).

Synthesis of 1-(5-bromo-2-ethyl-4-nitro-2H-pyrazol-3-ylamino)propan-2-ol (4-2)

A mixture of 3,5-dibromo-1-ethyl-4-nitro-1H-pyrazole (3) (20.0 g; 66.9 mmol), EtOH (100 ml) and 1-amino-2-propanol (25.1 g, 334.2 mmol) was refluxed for 15 hours. The reaction medium was concentrated to the maximum under reduced pressure and the excess 1-amino-2-propanol was then distilled off under vacuum. The oil obtained was suspended in DCM (100 ml) and water (100 ml). The aqueous phase was washed with DCM (100 ml). The combined organic phases were washed with water (50 ml) and were then dried over $NaSO_4$. After evaporating off the solvent under reduced pressure, a brown solid was obtained (19.1 g), which was purified by chromatography on silica gel (eluent: EtOAc/hexane). After recrystallization of the solid from an EtOAc/hexane mixture (13 ml/20 ml), the 1-(5-bromo-2-ethyl-4-nitro-2H-pyrazol-3-ylamino)propan-2-ol was obtained in the form of a yellow solid (7.1 g, 36%).

Melting point: 82.7-84.2° C. Elemental analysis ($C_8H_{13}N_4O_3Br$). Found: C, 32.80%; H, 4.36%; N, 27.12%; Br, 18.86%. Theory: C, 32.78%; H, 4.47%; N, 27.26%; Br, 19.11%. $^1$H-NMR (400 MHz, $CDCl_3$): 7.09 (1H, s, NH); 4.14 (2H, m, $CH_2CH_3$), 4.06 (1H, m, CH(OH)), 3.47 (1H, m, $CH_2NH$), 3.31 (1H, m, $CH_2NH$), 1.59 (1H, s, OH), 1.46 (3H, t, J=7.3 Hz, $CH_2CH_3$), 1.30 (3H, d, $CH(OH)CH_3$).

Synthesis of 2, N3-diethyl-2H-pyrazole-3,4-diamine hydrobromide (5-1)

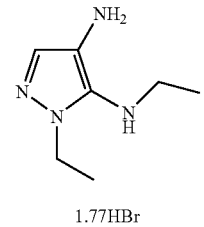

1.77HBr

A mixture of 1-(5-bromo-2-ethyl-4-nitro-2H-pyrazol-3-yl)ethylamine (4-1) (9.1 g; 35 mmol) in EtOH (500 ml) containing 10% Pd/C as catalyst (Johnson-Mattey Type 487, 2.0 g wet, 0.9 g dry weight) and hydrobromic acid (48%, 10.9 g, 80 mmol) was hydrogenated in an autoclave (11) at 11 bar for 15 hours. The catalyst was filtered off and washed with EtOH (50 ml), and the filtrate was evaporated under reduced pressure. Acetone was added under an inert atmosphere and with stirring. After stirring for 20 minutes, a white solid was obtained. After stirring for 1 hour, the precipitate formed was recovered by filtration and was washed with acetone (100 ml) under an inert atmosphere and then dried under vacuum (over $P_2O_5$) to give the 2,N3-diethyl-2H-pyrazole-3,4-diamine in the form of the hydrobromide (1.77 HBr), as a white solid (7.5 g, 69%).

Melting point: 190.6-192.2° C. Elemental analysis ($C_7H_{14}N_4$, 1.77 HBr). Found: C, 31.42%; H, 5.34%; N, 15.31%; Br, 45.70%. Theory: C, 28.27%; H, 5.34%; N, 18.83%; Br, 47.55% $^1$H-NMR (400 MHz, $d^6$-DMSO): 13.8 (2H, s, $NH_2$); 9.53 (1H, s, NH), 7.47 (1H, s, $H_{Ar}$), 3.98 (2H, q, J=7.0 Hz, $NH_2CH_3$), 3.07 (2H, m, $NHCH_2CH_3$), 1.27 (3H, t, J 7.0 Hz, $NCH_2CH_3$), 1.09 (3H, t, J=7.0 Hz, $NHCH_2CH_3$).

Synthesis of 1-(4-amino-2-ethyl-2H-pyrazol-3-ylamino)-propan-2-ol hydrobromide (5-2)

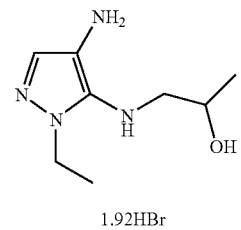

1.92HBr

A mixture of 1-(5-bromo-2-ethyl-4-nitro-2H-pyrazol-3-ylamino)propan-2-ol (4-2) (7.0 g; 23.9 mmol) in EtOH (500 ml) containing 10% Pd/C as catalyst (Johnson-Mattey Type 487, 1.6 g wet, 0.7 g dry weight) and hydrobromic acid (48%, 9.1 g, 54.0 mmol) was hydrogenated in a Parr autoclave (11) at 11 bar for 15 hours. The catalyst was removed by filtration and washed with EtOH (50 ml), and the filtrate was evaporated under reduced pressure (rotary evaporator, 45° C. water bath) to give an orange-red oil (14.2 g). Under an inert atmosphere, the oil was dissolved in hot ethanol (10 ml). After adding EtOAc (30 ml), the reaction mixture was cooled to 0-5° C. for 1 hour and a white precipitate formed. After filtration and drying, the 1-(4-amino-2-ethyl-2H-pyrazol-3-ylamino)propan-2-ol hydrobromide (1.92 HBr) was obtained in the form of a white solid (5.6 g, 67%).

Melting point: 180.0-182.4° C. Elemental analysis ($C_8H_{17.92}N_4OBr_{1.92}$). Found: C, 27.30%; H, 5.08%; N, 15.51%; Br, 47.35%. Theory: C, 27.77%; H, 5.24%; N, 16.19%; Br, 46.18%. $^1$H-NMR (400 MHz, d$^6$-DMSO): 9.59 (1H, $S_{broad}$, NH), 7.36 (1H, S, $H_{Ar}$), 3.97 (2H, q, J=7.3 Hz, NCH$_2$CH$_3$), 3.75 (1H, m, CH(OH)), 3.06 (1H, m, CH(OH)), 2.93 (2H, m, NHCH$_2$CH(OH)), 1.26 (3H, t, J=7.3 Hz, NCH$_2$CH$_3$), 1.11 (3H, d, J 6.6 Hz, CH(OH)CH$_3$).

EXAMPLES OF DYEING IN ALKALINE MEDIUM

The dye formulations below are prepared:

| | |
|---|---|
| 4,5-diaminopyrazole of formula (I) | $5 \times 10^{-3}$ mol |
| coupler | $5 \times 10^{-3}$ mol |
| oleyl alcohol polyglycerolated with 2 mol of glycerol | 4.0 g |
| oleyl alcohol polyglycerolated with 4 mol of glycerol, containing 78% active material (A.M.) | 5.7 g A.M. |
| oleic acid | 3.0 g |
| oleylamine containing 2 mol of ethylene oxide, sold under the trade name Ethomeen O12 by the company Akzo | 7.0 g |
| diethylaminopropyl laurylamino succinamate, sodium salt, at 55% A.M. | 3.0 g A.M. |
| oleyl alcohol | 5.0 g |
| oleic acid diethanolamide | 12.0 g |
| propylene glycol | 3.5 g |
| ethyl alcohol | 7.0 g |
| dipropylene glycol | 0.5 g |
| propylene glycol monomethyl ether | 9.0 g |
| sodium metabisulfite as an aqueous solution containing 35% A.M. | 0.455 g A.M. |
| ammonium acetate | 0.8 g |
| antioxidant, sequestering agent | qs |
| fragrance, preserving agent | qs |
| aqueous ammonia containing 20% NH$_3$ | 100 g |

The pH of the composition is 9.5
A.M. means "active material"

| Examples | Base | Coupler |
|---|---|---|
| 1 | 2,N3-diethyl-2H-pyrazole-3,4-diamine, 1.77 HBr (5-1) | 5-amino-6-chloro-2-methylphenol |
| 2 | 2,N3-diethyl-2H-pyrazole-3,4-diamine, 1.77 HBr (5-1) | 2-methyl-5-aminophenol |
| 3 | 2,N3-diethyl-2H-pyrazole-3,4-diamine, 1.77 HBr (5-1) | 1-β-hydroxyethoxy-2,4-diaminobenzene, 2HCl |
| 4 | 1-(4-amino-2-ethyl-2H-pyrazol-3-ylamino)propan-2-ol, 1.92 HBr (5-2) | 5-amino-6-chloro-2-methylphenol |
| 5 | 1-(4-amino-2-ethyl-2H-pyrazol-3-ylamino)propan-2-ol, 1.92 HBr (5-2) | 2-methyl-5-aminophenol |

-continued

| Examples | Base | Coupler |
|---|---|---|
| 6 | 1-(4-amino-2-ethyl-2H-pyrazol-3-ylamino)propan-2-ol, 1.92 HBr (5-2) | 1-β-hydroxyethoxy-2,4-diaminobenzene, 2HCl |

At the time of use, each dye composition is mixed, weight for weight, with a 20-volumes aqueous hydrogen peroxide solution (6% by weight), the pH of which has been adjusted to about 2.5 with orthophosphoric acid.

The mixture is applied to natural or permanent-waved grey hair containing 90% white hairs, at a rate of 5 g per 0.5 g of hair, for 30 minutes.

The hair is then rinsed, washed with a standard shampoo and dried.

The color of the locks was evaluated in the L*a*b* system, on white and permanent-waved hair, using a Minolta CM 2002 spectrophotometer.

In the L*a*b* space, the lightness is indicated by the value L* on a scale from 0 to 100, while the chromatic data is expressed by a* and b* which indicate two color axes, a* the red-green axis and b* the yellow-blue axis.

According to this system, the higher the value of L, the paler and less intense the color. Conversely, the lower the value of L, the darker or more intense the color.

| | Natural white hair | | | Permanent-waved white hair | | |
|---|---|---|---|---|---|---|
| Example | L* | a* | b* | L* | a* | b* |
| Example 1 | 35.5 | 29.8 | −1.34 | 28.2 | 30.6 | −0.07 |
| Example 2 | 42.2 | 26.6 | 7.97 | 34.7 | 30.5 | 8.02 |
| Example 3 | 30.0 | 12.0 | −8.68 | 22.2 | 10.5 | −7.5 |
| Example 4 | 40.7 | 27.4 | 1.12 | 30.7 | 30.7 | 1.01 |
| Example 5 | 43.6 | 27.0 | 9.32 | 33.0 | 31.7 | 11.3 |
| Example 6 | 33.3 | 12.8 | −6.7 | 22.8 | 11.9 | −7.11 |

The 4,5-diaminopyrazoles according to the invention thus make it possible to obtain strong and chromatic shades at alkaline pH.

The invention claimed is:

1. A composition for the oxidation dyeing of keratin fibers, comprising, in a medium suitable for dyeing, at least one oxidation base chosen from diaminopyrazole compounds chosen from:

| Structure | Name |
|---|---|
| 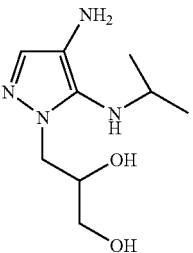 | 3-(4-amino-5-isopropylamino-pyrazol-1-yl)propane-1,2-diol |

| Structure | Name |
|---|---|
| 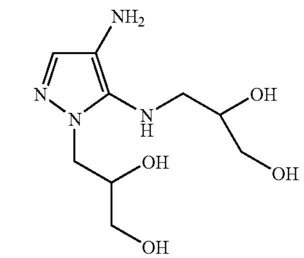 | 3-[4-amino-5-(2,3-dihydroxypropylamino)-pyrazol-1-yl]propane-1,2-diol |
| 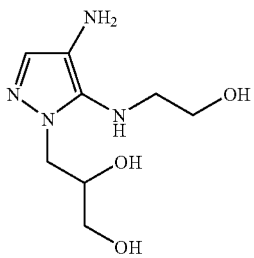 | 3-[4-amino-5-(2-hydroxyethylamino)pyrazol-1-yl]propane-1,2-diol |
| 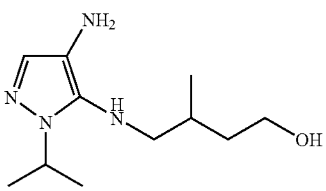 | 4-(4-amino-2-isopropyl-2H-pyrazol-3-ylamino)-3-methylbutan-1-ol |
| | 3-(4-amino-5-ethylaminopyrazol-1-yl)propane-1,2-diol |
| 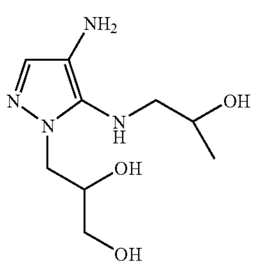 | 3-[4-amino-5-(2-hydroxypropylamino)-pyrazol-1-yl]propane-1,2-diol |
| 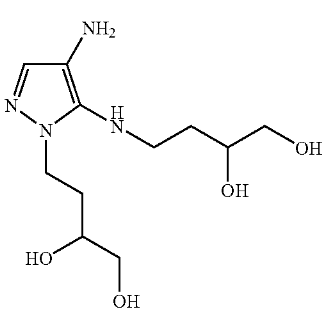 | 4-[4-amino-5-(3,4-dihydroxybutylamino)-pyrazol-1-yl]butane-1,2-diol |

| Structure | Name |
|---|---|
| 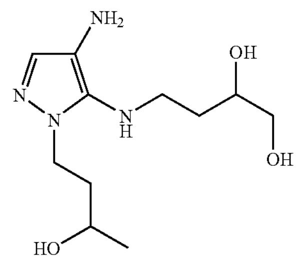 | 4-[4-amino-2-(3-hydroxybutyl)-2H-pyrazol-3-ylamino]-butane-1,2-diol |
| | 4-[4-amino-2-ethyl-2H-pyrazol-3-ylamino]-butane-2,3-diol |
| | 1-(4-amino-5-ethylaminopyrazol-1-yl)butane-2,3-diol |
| 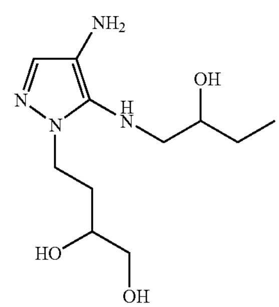 | 4-[4-amino-5-(2-hydroxybutylamino)pyrazol-1-yl]butane-1,2-diol |
| 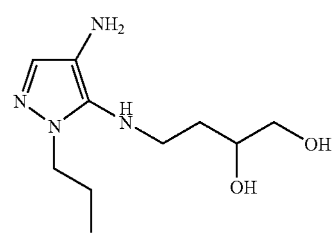 | 4-(4-amino-2-propyl-2H-pyrazol-3-ylamino)-butane-1,2-diol |
| | 4-(4-amino-5-propylaminopyrazol-1-yl)butane-1,2-diol |

| Structure | Name |
|---|---|
| 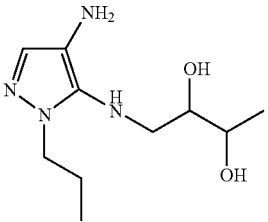 | 1-(4-amino-2-propyl-2H-pyrazol-3-ylamino)-butane-2,3-diol |
| 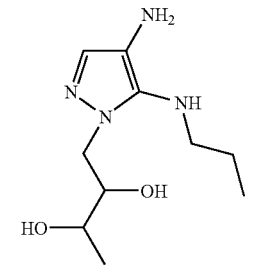 | 4-(4-amino-5-propyl-aminopyrazol-1-yl)butane-1,2-diol |
| 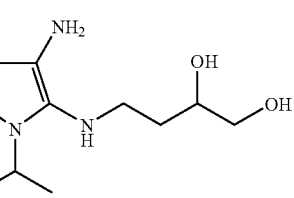 | 4-(4-amino-2-isopropyl-2H-pyrazol-3-ylamino)-butane-1,2-diol |
| 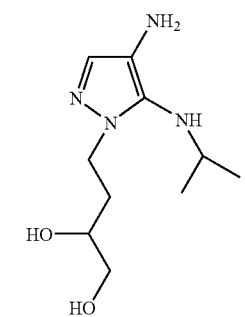 | 4-(4-amino-5-isopropylamino-pyrazol-1-yl)butane-1,2-diol |
| 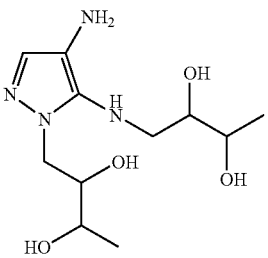 | 1-[4-amino-5-(2,3-dihydroxybutylamino)-pyrazol-1-yl]butane-2,3-diol |
| 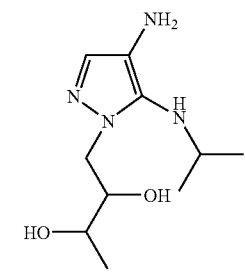 | 4-(4-amino-5-isopropylamino-pyrazol-1-yl)butane-1,2-diol |

| Structure | Name |
|---|---|
| 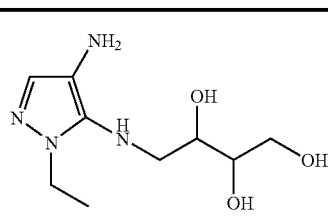 | 4-(4-amino-2-ethyl-2H-pyrazol-3-ylamino)-butane-1,2,3-triol |
| 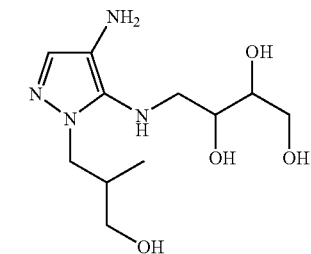 | 4-[4-amino-2-(3-hydroxy-2-methylpropyl)-2H-pyrazol-3-ylamino]-butane-1,2,3-triol |
| 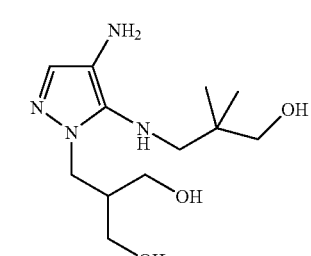 | 2-[4-amino-5-(3-hydroxy-2,2-dimethylpropyl-amino)pyrazol-1-ylmethyl]-propane-1,3-diol |
| 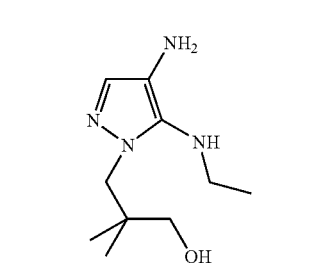 | 3-(4-amino-5-ethyl-aminopyrazol-1-yl)-2,2-dimethylpropan-1-ol |
| 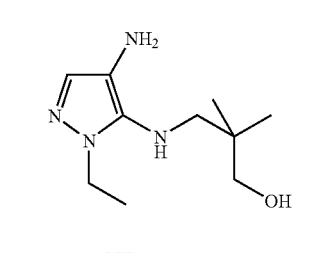 | 3-(4-amino-2-ethyl-2H-pyrazol-3-ylamino)-2,2-dimethyl-propan-1-ol |
| 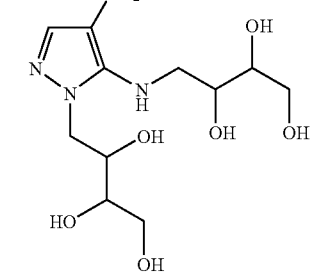 | 4-[4-amino-5-(2,3,4-trihydroxybutyl-amino)pyrazol-1-yl]butane-1,2,3-triol |

-continued

| Structure | Name |
|---|---|
| 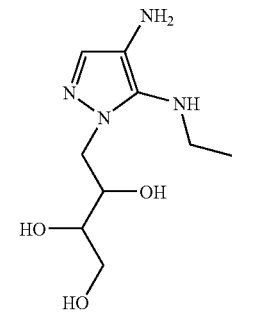 | 4-(4-amino-5-ethyl-aminopyrazol-1-yl)butane-1,2,3-triol |
| 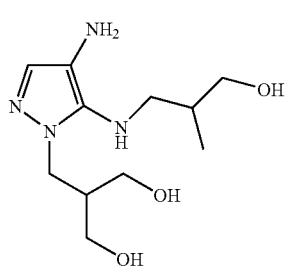 | 2-[4-amino-5-(3-hydroxy-2-methylpropylamino)-pyrazol-1-ylmethyl]-propane-1,3-diol |
| 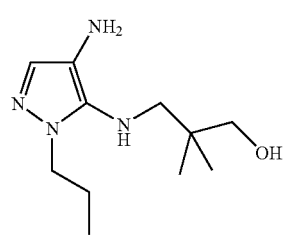 | 3-(4-amino-2-propyl-2H-pyrazol-3-ylamino)-2,2-dimethyl-propan-1-ol |
| 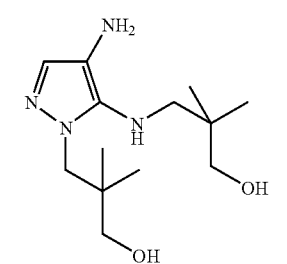 | 3-[4-amino-5-(3-hydroxy-2,2-dimethylpropyl-amino)pyrazol-1-yl]-2,2-dimethylpropan-1-ol |
| 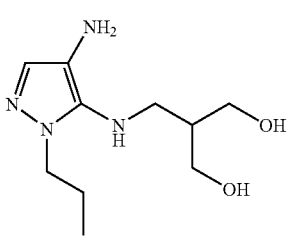 | 2-[(4-amino-2-propyl-2H-pyrazol-3-ylamino)-methyl]-propane-1,3-diol |
| 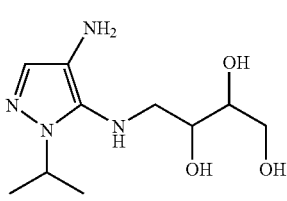 | 4-(4-amino-2-isopropyl-2H-pyrazol-3-ylamino)-butane-1,2,3-triol |

-continued

| Structure | Name |
|---|---|
| 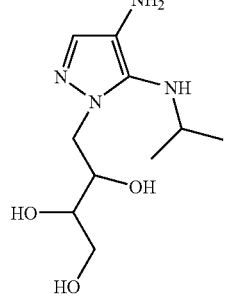 | 4-(4-amino-5-isopropylamino-pyrazol-1-yl)butane-1,2,3-triol |
| 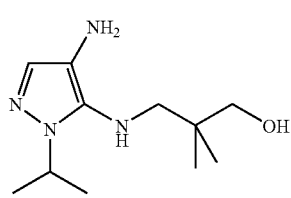 | 3-(4-amino-2-isopropyl-2H-pyrazol-3-ylamino)-2,2-dimethyl-propan-1-ol |
| 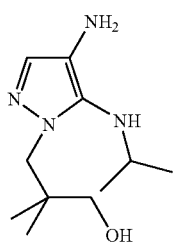 | 3-(4-amino-5-isopropylamino-pyrazol-1-yl)-2,2-dimethyl-propan-1-ol |
| 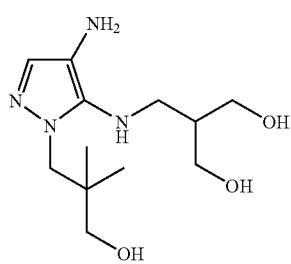 | 2-{[4-amino-2-(3-hydroxy-2,2-dimethylpropyl)-2H-pyrazol-3-ylamino]-methyl}proane-1,3-diol |
| 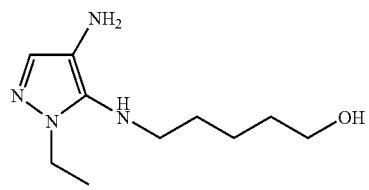 | 5-(4-amino-2-ethyl-2H-pyrazol-3-ylamino)-pentan-1-ol |
| 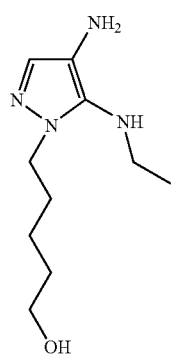 | 5-(4-amino-5-ethyl-aminopyrazol-1-yl)pentan-1-ol |

| Structure | Name |
|---|---|
| | 1-(4-amino-2-ethyl-2H-pyrazol-3-ylamino)-3-methylbutan-2-ol |
| | 1-[4-amino-5-(2-hydroxy-3-methylbutylamino)-pyrazol-1-yl]pentan-2-ol |
| | 1-[4-amino-5-(2-hydroxy-pentylamino)-pyrazol-1-yl]pentan-2-ol |
| | 1-(4-amino-5-ethylamino-pyrazol-1-yl)pentan-2-ol |
| | 5-(4-amino-2-propyl-2H-pyrazol-3-ylamino)-pentan-1-ol |
| 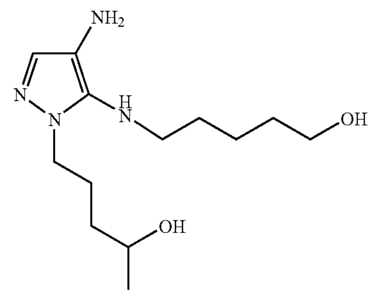 | 5-[4-amino-2-(4-hydroxy-pentyl)-2H-pyrazol-3-ylamino]-pentan-1-ol |
| 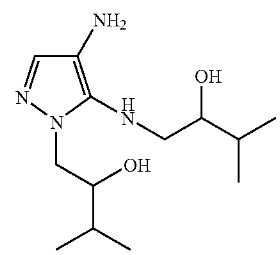 | 1-[4-amino-5-(2-hydroxy-3-methylbutylamino)-pyrazol-1-yl]-3-methylbutan-2-ol |
| 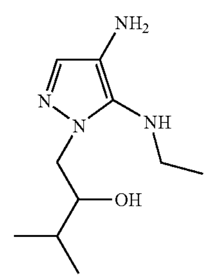 | 1-(4-amino-5-ethylamino-pyrazol-1-yl)-3-methylbutan-2-ol |
| 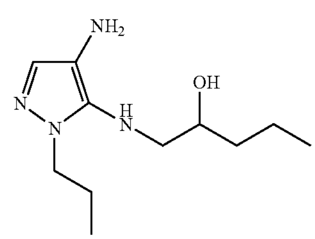 | 1-(4-amino-2-propyl-2H-pyrazol-3-ylamino)-pentan-2-ol |
| 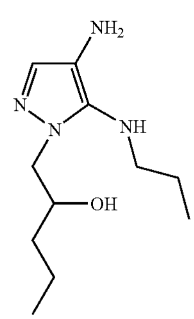 | 1-(4-amino-5-propylamino-pyrazol-1-yl)pentan-2-ol |
| 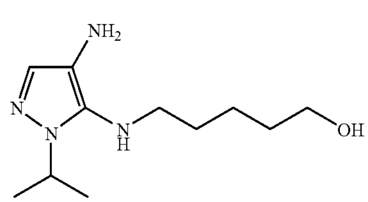 | 5-(4-amino-2-isopropyl-2H-pyrazol-3-ylamino)-pentan-1-ol |

-continued

| Structure | Name |
|---|---|
| 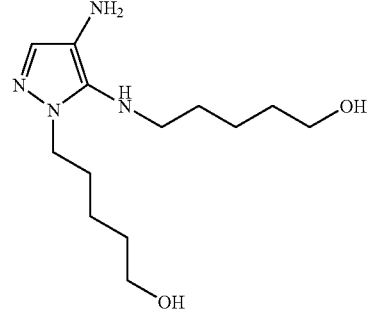 | 5-[4-amino-5-(5-hydroxypentylamino)-pyrazol-1-yl]pentan-1-ol |
| 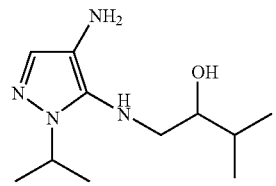 | 1-(4-amino-2-isopropyl-2H-pyrazol-3-ylamino)-3-methylbutan-2-ol |
| 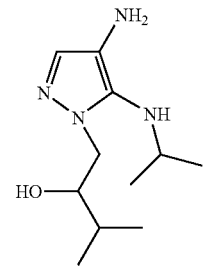 | 1-(4-amino-5-propylamino-pyrazol-1-yl)-3-methylbutan-2-ol |
| 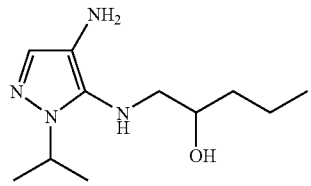 | 1-(4-amino-2-isopropyl-2H-pyrazol-3-ylamino)-pentan-2-ol |
| 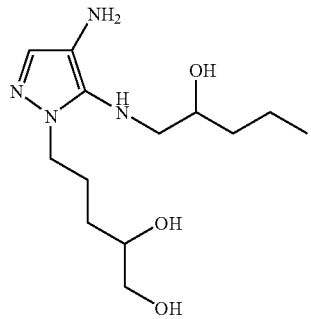 | 5-[4-amino-5-(3-hydroxypentylamino)-pyrazol-1-yl]-pentane-1,2-diol |
| 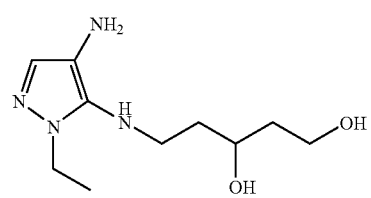 | 5-(4-amino-2-ethyl-2H-pyrazol-3-ylamino)-pentane-1,3-diol |

-continued

| Structure | Name |
|---|---|
| 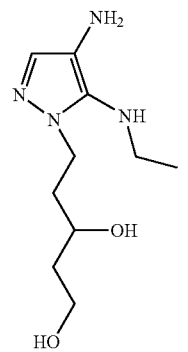 | 5-(4-amino-5-ethyl-aminopyrazol-1-yl)pentane-1,3-diol |
| 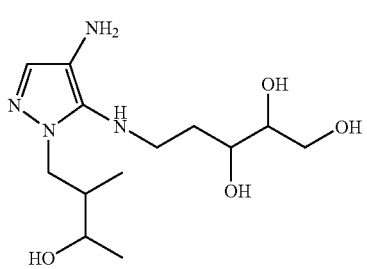 | 5-[4-amino-2-(3-hydroxy-2-methylbutyl)-2H-pyrazol-3-ylamino]-pentane-1,2,3-triol |
| 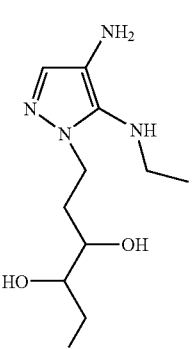 | 5-(4-amino-5-ethylamino-pyrazol-1-yl)pentane-1,2,3-triol |
| 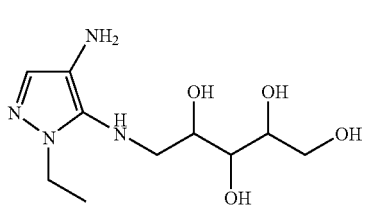 | 5-(4-amino-2-ethyl-2H-pyrazol-3-ylamino)-pentane-1,2,3,4-tetraol |
| 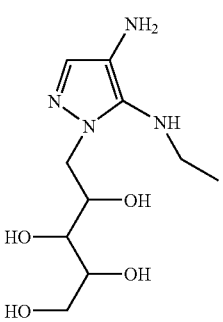 | 5-(4-amino-5-ethylamino-pyrazol-1-yl)pentane-1,2,3,4-tetraol |

-continued

| Structure | Name |
|---|---|
| 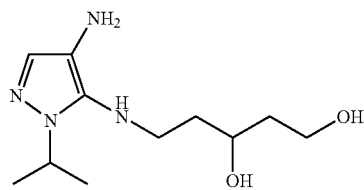 | 5-(4-amino-2-isopropyl-2H-pyrazol-3-ylamino)-pentane-1,3-diol |
| 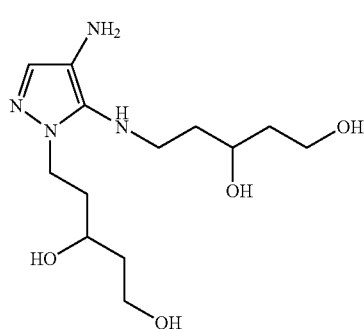 | 5-[4-amino-5-(3,5-dihydroxypentylamino)-pyrazol-1-yl]pentane-1,3-diol |
| 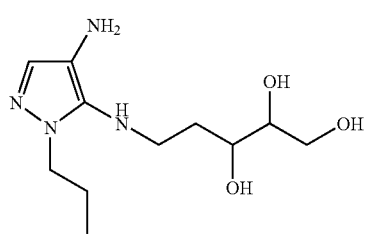 | 5-(4-amino-2-propyl-2H-pyrazol-3-ylamino)-pentane-1,2,3-triol |
| 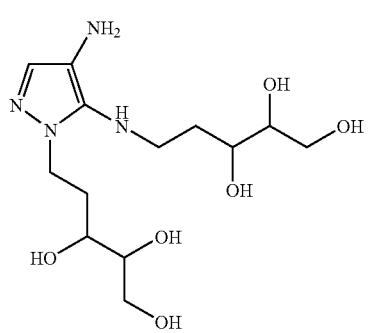 | 5-[4-amino-5-(3,4,5-trihydroxy-pentylamino)-pyrazol-1-yl]pentane-1,2,3-triol |
| 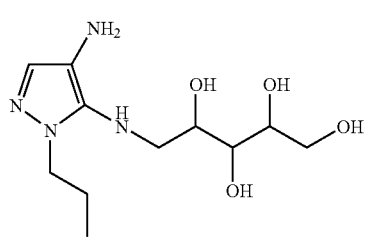 | 5-(4-amino-2-propyl-2H-pyrazol-3-ylamino)-pentane-1,2,3,4-tetraol |

-continued

| Structure | Name |
|---|---|
| 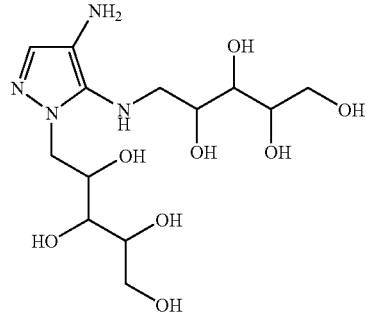 | 5-[4-amino-5-(2,3,4,5-tetra-hydroxypentyl-amino)pyrazol-1-yl]pentane-1,2,3,4-tetraol |
| 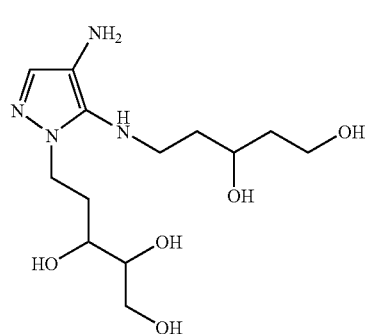 | 5-[4-amino-5-(3,5-dihydroxypentylamino)-pyrazol-1-yl]pentane-1,2,3-triol |
| 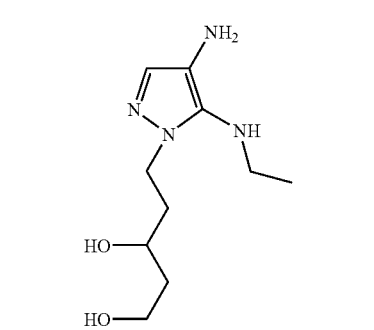 | 5-(4-amino-5-ethylamino-pyrazol-1-yl)pentane-1,3-diol |
| 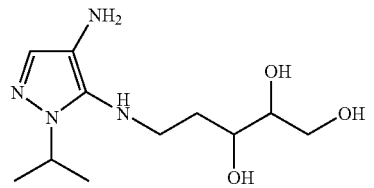 | 5-(4-amino-2-isopropyl-2H-pyrazol-3-ylamino)-pentane-1,2,3-triol |
| 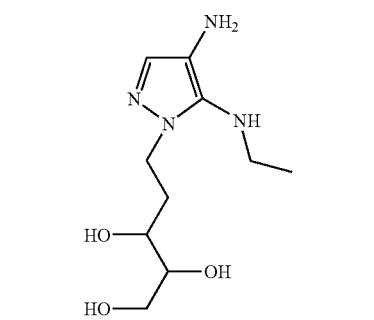 | 5-(4-amino-5-ethylamino-pyrazol-1-yl)pentane-1,2,3-triol |

-continued

| Structure | Name |
|---|---|
| [structure: 5-(4-amino-2-isopropyl-2H-pyrazol-3-ylamino)pentane-1,2,3,4-tetraol] | 5-(4-amino-2-isopropyl-2H-pyrazol-3-ylamino)-pentane-1,2,3,4-tetraol |
| [structure: 5-[4-amino-2-(2-hydroxymethylbutyl)-2H-pyrazol-3-ylamino]pentane-1,2,3,4-tetraol] | 5-[4-amino-2-(2-hydroxymethylbutyl)-2H-pyrazol-3-ylamino]-pentane-1,2,3,4-tetraol | and the physiologically acceptable salts thereof.

2. The composition according to claim 1, wherein the at least one diaminopyrazole compound is chosen from:
- 3-(4-amino-5-isopro-pylamino-pyrazol-1-yl)prepane-1,2-diol;
- 3-[4-amino-5-(2,3-di-hydroxypro-pylamino)-pyrazol-1-yl]prepane-1,2-diol;
- 4-(4-amino-2-iso-propyl-2H-pyrazol-3-ylamino)-butane-1,2,3-triol;
- 3[4-amino5-(2-hy-droxyethyl-amino)-pyrazol-1-yl]-propane-1,2-diol;
- 4-(4-amino-2-ethyl-2H-pyrazol-3-ylamino)-butane-1,2,3-triol;
- 4-(4-amino-5-ethyl-aminopyra-zol-1-yl)-butane-1,2,3-triol;
- 3-(4-amino-5-ethyl-amino-pyrazol-1-yl)propane-1,2-diol;
- 3-[4-amino-5-(2-hydroxypro-pylamino)-pyrazol-1-yl]propane-1,2-diol;
- 4-[4-amino-5-(2,3,4-trihydroxy-butyl-amino)pyra-zol-1-yl]-butane-1,2,3-triol;
- 4-(4-amino-5-isopro-pylamino-pyrazol-1-yl )butane-1,2,3-triol, and the physiologically acceptable salts thereof.

3. The composition according to claim 1, wherein the at least one diaminopyrazole compound is chosen from:
- 3-(4-amino-5-ethylaminopyrazol-1-yl)propane-1,2-diol and the physiologically acceptable acid salts thereof.

4. The composition according to claim 1, wherein said at least one oxidation base is present in an amount ranging from 0.001% to 10% by weight, relative to the total weight of the composition.

5. The composition according to claim 4, wherein said at least one oxidation base is present in an amount ranging from 0.05% to 6% by weight, relative to the total weight of the composition.

6. The composition according to claim 5, wherein said at least one oxidation base is present in an amount ranging from 0.1% to 3% by weight, relative to the total weight of the composition.

7. The composition according to claim 1, wherein the medium suitable for dyeing comprises water or of a mixture of water and at least one organic solvent chosen from $C_1$-$C_4$ lower alkanols, polyols, polyols ethers, and aromatic alcohols.

8. The composition according to claim 1, said composition having a pH ranging from 3 to 12.

9. The composition according to claim 1, comprising at least one additional oxidation base chosen from para-phenylenediamines, bis(phenyl)alkylenediamines, para-aminophenols, ortho-aminophenols and heterocyclic bases other than the substituted N3-diaminopyrazole as defined in claim 1, and acid addition salts thereof.

10. The composition according to claim 9, wherein said at least one additional oxidation base is present an amount ranging from 0.0005% to 12% by weight, relative to the total weight of the composition.

11. The composition according to claim 1, further comprising at least one coupler and/or at least one direct dye.

12. The composition according to claim 11, wherein said at least one coupler is chosen from meta-phenylenediamines, meta-aminophenols, meta-diphenols, mono-or polyhydroxylated naphthalene derivatives and heterocyclic couplers, and the acid addition salts thereof.

13. The composition according to claim 12, further comprising at least one coupler chosen from 5-N-([β]-hydroxyethyl)amino-2-methyl-phenol, 6-chloro-2-methyl-5-aminophenol, 3-aminophenol, 1,3-dihydroxy-2-methylbenzene, 4-chloro-1,3-dihyd roxybenzene, 2,4-diamino-1-([β]-hydroxy-ethyloxy)benzene, 2-amino-4-([β]-hydroxyethylamino)-1-methoxybenzene, 1,3-diaminobenzene, 1,3-bis(2,4-di-aminophenoxy)propane, 3-ureidoaniline, 3-ureido-1-di-methylaminobenzene, sesamol, 1-[beta]-hydroxyethylamino-3,4-methylenedioxybenzene,[α]-naphthol, 2-methyl-1-naphthol, 6-hydroxyindole, 4-hydroxyindole, 4-hydroxy-N-methylindole, 2-amino-3-hydroxypyridme, 6-hydroxybenzomorpholine, 3,5-diamino-2,6-dimethoxy-pyridine, 1-N-([β]-hydroxyethyl)amino-3,4-methylene-d ioxybenzene and 2,6-bis([β]-hydroxyethylamino)toluene, and the addition salts thereof.

14. The composition according to claim 11, wherein said at least one coupler is present in an amount ranging from 0.0001% to 10% by weight, relative to the total weight of the composition.

15. The composition according to claim 1, wherein the physiologically acceptable salts are chosen from hydrochlorides, hydrobromides, sulfates, tartrates, lactates and acetates.

16. The composition according to claim 1, wherein said keratin fibers are human hair.

17. A process for dyeing keratin fibers, comprising applying to the keratin fibers a composition for the oxidation dyeing of keratin fibers, comprising, in a medium suitable for dying, at least one oxidation base, chosen from diaminopyrazole compounds chosen from:

| Structure | Name |
|---|---|
| [structure: 4-(4-amino-2-isopropyl-2H-pyrazol-3-ylamino)-3-methylbutan-1-ol] | 4-(4-amino-2-isopropyl-2H-pyrazol-3-ylamino)-3-methylbutan-1-ol |

| Structure | Name |
|---|---|
| | 3-(4-amino-5-ethylamino-pyrazol-1-yl)propane-1,2-diol |
| | 3-(4-amino-5-isopropylamino-pyrazol-1-yl)propane-1,2-diol |
| | 3-[4-amino-5-(2,3-dihydroxypropylamino)-pyrazol-1-yl]propane-1,2-diol |
| | 3-[4-amino-5-(2-hydroxyethylamino)pyrazol-1-yl]propane-1,2-diol |
| | 4-[4-amino-5-(2-hydroxybutylamino)pyrazol-1-yl]butane-1,2-diol |
| | 3-[4-amino-5-(2-hydroxypropylamino)-pyrazol-1-yl]propane-1,2-diol |
| | 4-[4-amino-5-(3,4-dihydroxybutylamino)-pyrazol-1-yl]butane-1,2-diol |
| | 4-[4-amino-2-(3-hydroxybutyl)-2H-pyrazol-3-ylamino]-butane-1,2-diol |
| | 1-(4-amino-2-ethyl-2H-pyrazol-3-ylamino)-butane-2,3-diol |
| | 1-(4-amino-5-ethylaminopyrazol-1-yl)butane-2,3-diol |
| | 4-(4-amino-2-ethyl-2H-pyrazol-3-ylamino)-butane-1,2,3-triol |

| Structure | Name |
|---|---|
| 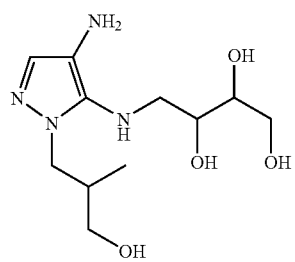 | 4-[4-amino-2-(3-hydroxy-2-methylpropyl)-2H-pyrazol-3-ylamino]-butane-1,2,3-triol |
| 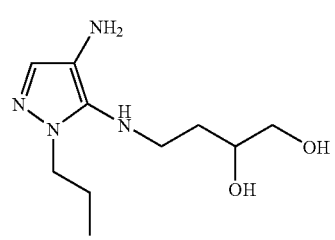 | 4-(4-amino-2-propyl-2H-pyrazol-3-ylamino)-butane-1,2-diol |
| 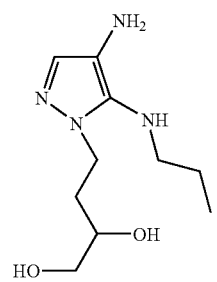 | 4-(4-amino-5-propyl-aminopyrazol-1-yl)butane-1,2-diol |
| 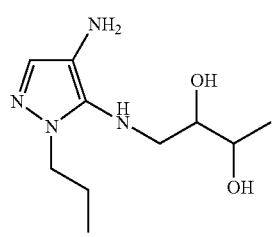 | 1-(4-amino-2-propyl-2H-pyrazol-3-ylamino)-butane-2,3-diol |
| 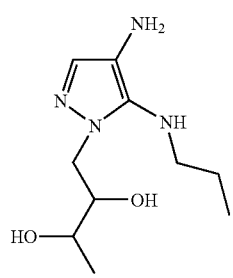 | 4-(4-amino-5-propyl-aminopyrazol-1-yl)butane-1,2-diol |

| Structure | Name |
|---|---|
| 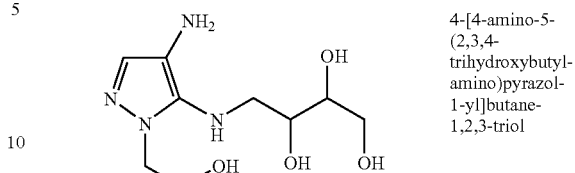 | 4-[4-amino-5-(2,3,4-trihydroxybutyl-amino)pyrazol-1-yl]butane-1,2,3-triol |
| 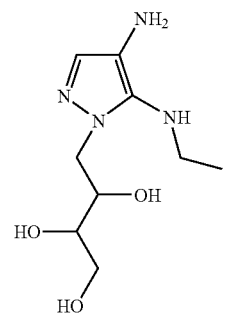 | 4-(4-amino-5-ethyl-aminopyrazol-1-yl)butane-1,2,3-triol |
| 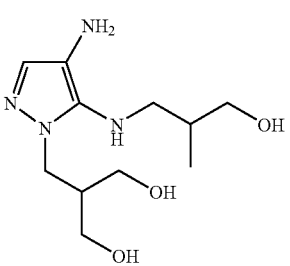 | 2-[4-amino-5-(3-hydroxy-2-methylpro-pylamino)-pyrazol-1-ylmethyl]-propane-1,3-diol |
| 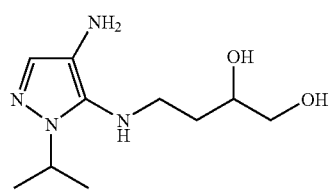 | 4-(4-amino-2-isopropyl-2H-pyrazol-3-ylamino)-butane-1,2-diol |
| 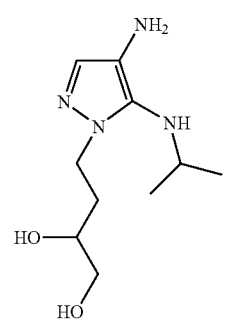 | 4-(4-amino-5-isopro-pylamino-pyrazol-1-yl)butane-1,2-diol |

| Structure | Name |
|---|---|
| 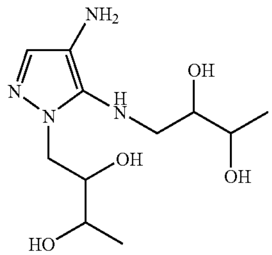 | 1-[4-amino-5-(2,3-dihydroxybutylamino)-pyrazol-1-yl]butane-2,3-diol |
| | 4-(4-amino-5-isopropylaminopyrazol-1-yl)butane-1,2-diol |
| 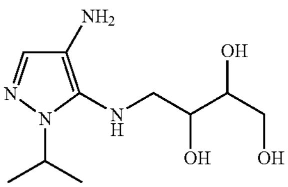 | 4-(4-amino-2-isopropyl-2H-pyrazol-3-ylamino)-butane-1,2,3-triol |
| | 4-(4-amino-5-isopropylaminopyrazol-1-yl)butane-1,2,3-triol |
| | 2-[4-amino-5-(3-hydroxy-2,2-dimethylpropylamino)pyrazol-1-ylmethyl]-propane-1,3-diol |
| 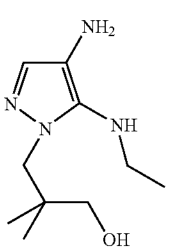 | 3-(4-amino-5-ethyl-aminopyrazol-1-yl)-2,2-dimethylpropan-1-ol |

| Structure | Name |
|---|---|
| 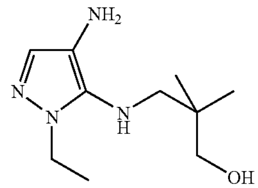 | 3-(4-amino-2-ethyl-2H-pyrazol-3-ylamino)-2,2-dimethyl-propan-1-ol |
| 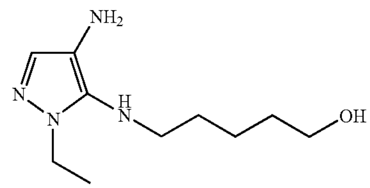 | 5-(4-amino-2-ethyl-2H-pyrazol-3-ylamino)-pentan-1-ol |
| | 5-(4-amino-5-ethylaminopyrazol-1-yl)pentan-1-ol |
| 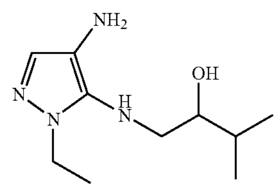 | 1-(4-amino-2-ethyl-2H-pyrazol-3-ylamino)-3-methylbutan-2-ol |
| 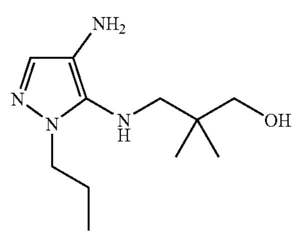 | 3-(4-amino-2-propyl-2H-pyrazol-3-ylamino)-2,2-dimethyl-propan-1-ol |
| | 3-[4-amino-5-(3-hydroxy-2,2-dimethylpropylamino)pyrazol-1-yl]-2,2-dimethylpropan-1-ol |

-continued

| Structure | Name |
|---|---|
| 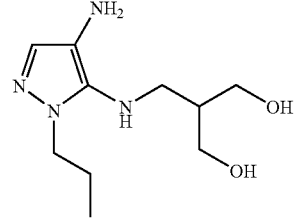 | 2-[(4-amino-2-propyl-2H-pyrazol-3-ylamino)-methyl]-propane-1,3-diol |
| 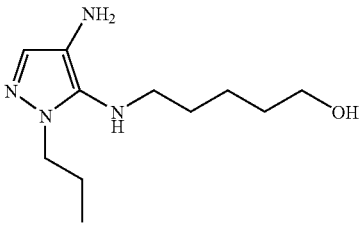 | 5-(4-amino-2-propyl-2H-pyrazol-3-ylamino)-pentan-1-ol |
| 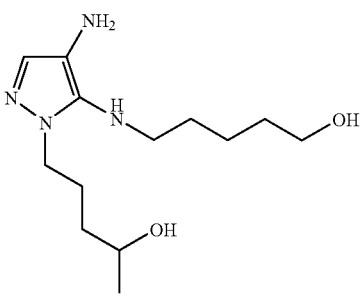 | 5-[4-amino-2-(4-hydroxy-pentyl)-2H-pyrazol-3-ylamino]-pentan-1-ol |
| 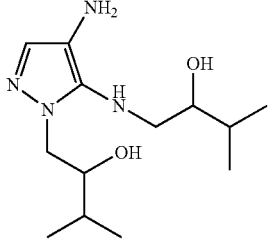 | 1-[4-amino-5-(2-hydroxy-3-methylbutylamino)-pyrazol-1-yl]-3-methylbutan-2-ol |
| 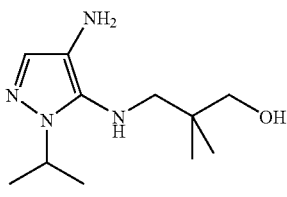 | 3-(4-amino-2-isopropyl-2H-pyrazol-3-ylamino)-2,2-dimethyl-propan-1-ol |
| 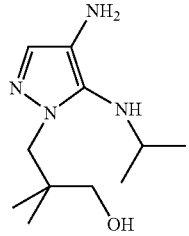 | 3-(4-amino-5-isopropylamino-pyrazol-1-yl)-2,2-dimethyl-propan-1-ol |

-continued

| Structure | Name |
|---|---|
| 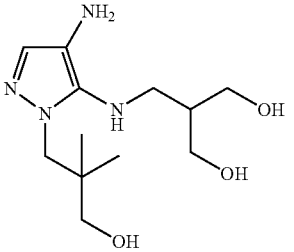 | 2-{[4-amino-2-(3-hydroxy-2,2-dimethylpropyl)-2H-pyrazol-3-ylamino]-methyl}proane-1,3-diol |
| 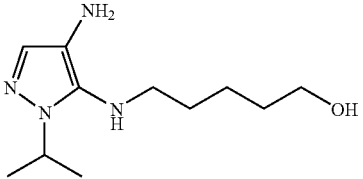 | 5-(4-amino-2-isopropyl-2H-pyrazol-3-ylamino)-pentan-1-ol |
| 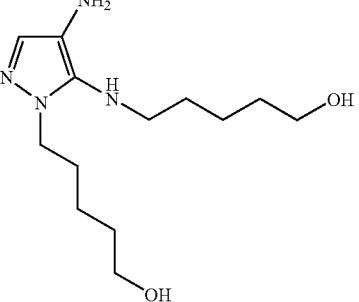 | 5-[4-amino-5-(5-hydroxypentylamino)-pyrazol-1-yl]pentan-1-ol |
| 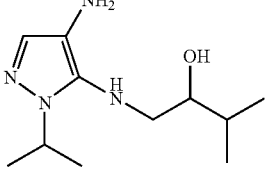 | 1-(4-amino-2-isopropyl-2H-pyrazol-3-ylamino)-3-methylbutan-2-ol |
| 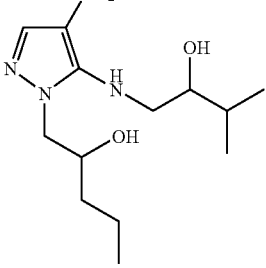 | 1-[4-amino-5-(2-hydroxy-3-methylbutylamino)-pyrazol-1-yl]pentan-2-ol |
| 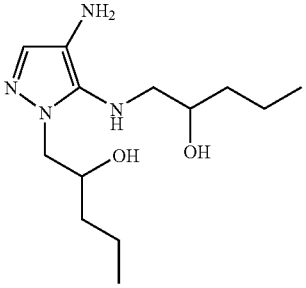 | 1-[4-amino-5-(2-hydroxy-pentylamino)-pyrazol-1-yl]pentan-2-ol |

-continued

| Structure | Name |
|---|---|
| 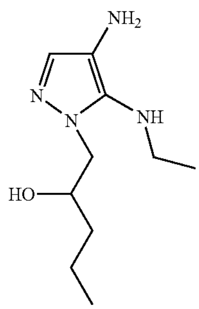 | 1-(4-amino-5-ethylamino-pyrazol-1-yl)pentan-2-ol |
| 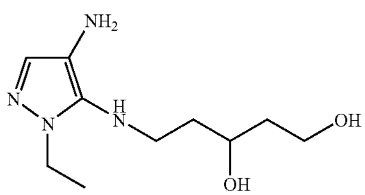 | 5-(4-amino-2-ethyl-2H-pyrazol-3-ylamino)-pentane-1,3-diol |
| 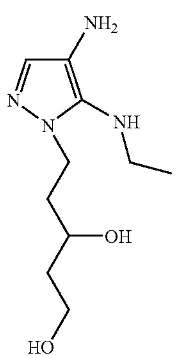 | 5-(4-amino-5-ethyl-aminopyrazol-1-yl)pentane-1,3-diol |
| 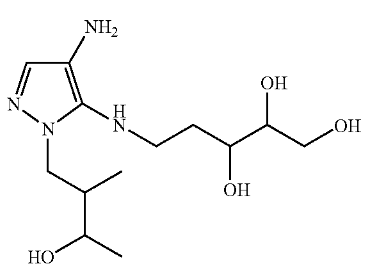 | 5-[4-amino-2-(3-hydroxy-2-methylbutyl)-2H-pyrazol-3-ylamino]-pentane-1,2,3-triol |
| 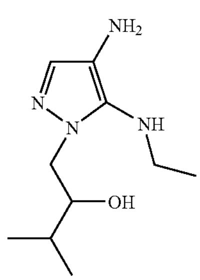 | 1-(4-amino-5-ethylamino-pyrazol-1-yl)-3-methylbutan-2-ol |

-continued

| Structure | Name |
|---|---|
| 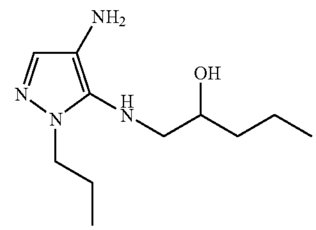 | 1-(4-amino-2-propyl-2H-pyrazol-3-ylamino)-pentan-2-ol |
| 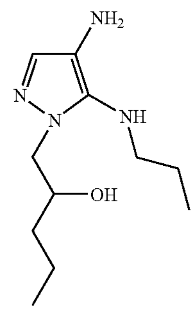 | 1-(4-amino-5-propylamino-pyrazol-1-yl)pentan-2-ol |
| 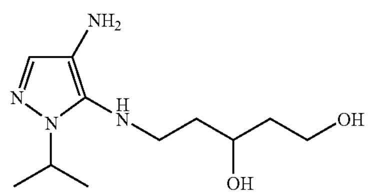 | 5-(4-amino-2-isopropyl-2H-pyrazol-3-ylamino)-pentane-1,3-diol |
| 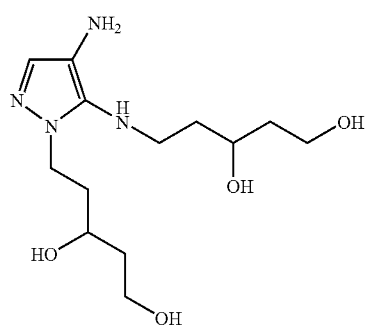 | 5-[4-amino-5-(3,5-di-hydroxypen-tylamino)-pyrazol-1-yl]pentane-1,3-diol |
| 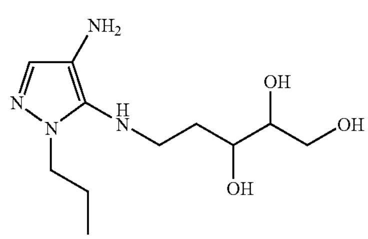 | 5-(4-amino-2-propyl-2H-pyrazol-3-ylamino)-pentane-1,2,3-triol |
| 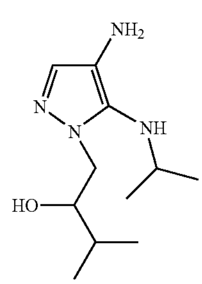 | 1-(4-amino-5-propylamino-pyrazol-1-yl)-3-methylbutan-2-ol |

| Structure | Name |
|---|---|
| 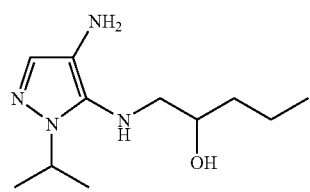 | 1-(4-amino-2-isopropyl-2H-pyrazol-3-ylamino)-pentan-2-ol |
| 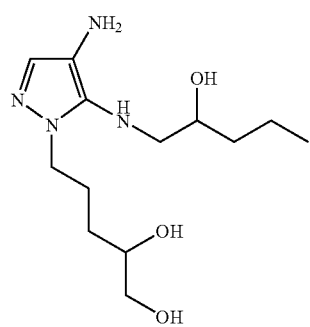 | 5-[4-amino-5-(3-hydroxypentylamino)-pyrazol-1-yl]-pentane-1,2-diol |
| 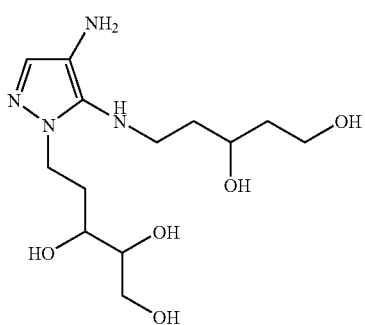 | 5-[4-amino-5-(3,5-dihydroxypentylamino)-pyrazol-1-yl]pentane-1,2,3-triol |
| 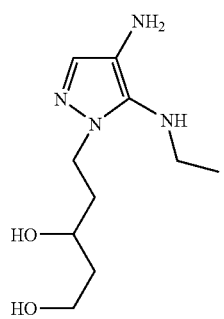 | 5-(4-amino-5-ethylamino-pyrazol-1-yl)pentane-1,3-diol |
| 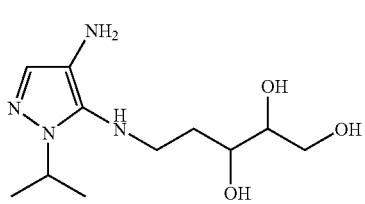 | 5-(4-amino-2-isopropyl-2H-pyrazol-3-ylamino)-pentane-1,2,3-triol |

| Structure | Name |
|---|---|
| 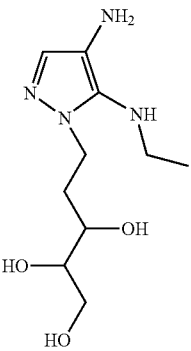 | 5-(4-amino-5-ethylamino-pyrazol-1-yl)pentane-1,2,3-triol |
| 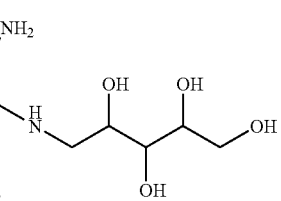 | 5-(4-amino-2-ethyl-2H-pyrazol-3-ylamino)-pentane-1,2,3,5-tetraol |
| 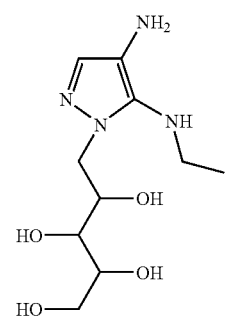 | 5-(4-amino-5-ethylamino-pyrazol-1-yl)pentane-1,2,3,4-tetraol |
| 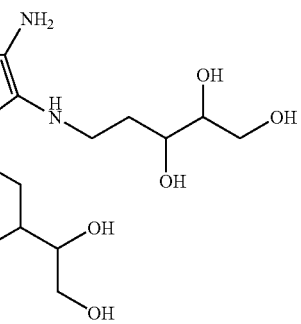 | 5-[4-amino-5-(3,4,5-trihydroxypentylamino)-pyrazol-1-yl]pentane-1,2,3-triol |
| 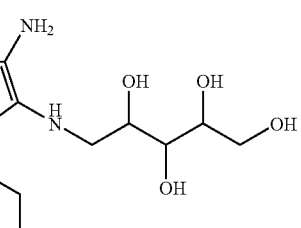 | 5-(4-amino-2-propyl-2H-pyrazol-3-ylamino)-pentane-1,2,3,4-tetraol |

| Structure | Name |
|---|---|
| (structure) | 5-[4-amino-5-(2,3,4,5-tetra-hydroxypentyl-amino)pyrazol-1-yl]pentane-1,2,3,4-tetraol |
| (structure) | 5-(4-amino-5-ethylamino-pyrazol-1-yl)pentane-1,2,3-triol |
| (structure) | 5-(4-amino-2-isopropyl-2H-pyrazol-3-ylamino)-pentane-1,2,3,4-tetraol |
| (structure) | 5-[4-amino-2-(2-hydroxymethylbutyl)-2H-pyrazol-3-ylamino]-pentane-1,2,3,4-tetraol | and the physiologically acceptable salts,
wherein said composition is applied to the keratin fibers for a period of time that is sufficient to develop the desired color, either in air or using an oxidizing agent.

18. The process according to claim 17, wherein the at least one diaminopyrazole compound is chosen from:

3-(4-amino-5-isopro-pylamino-pyrazol-1-yl)propane-1,2-diol;

3-[4-amino-5-(2,3-di-hydroxypro-pylamino)-pyrazol-1-yl]propane-1,2-diol;

4-(4-amino-2-iso-propyl-2H-pyrazol-3-ylamino)-butane-1,2,3-triol;

3-[4-amino5-(2-hy-droxyethyl-amino)-pyrazol-1-yl]-propane-1,2-diol;

4-(4-amino-2-ethyl-2H-pyrazol-3-ylamino)-butane-1,2,3-triol;

4-(4-amino-5-ethyl-aminopyra-zol-1-yl)-butane-1,2,3-triol;

3-(4-amino-5-ethyl-amino-pyrazol-1-yl)propane-1,2-diol;

3-[4-amino-5-(2-hydroxypro-pylamino)-pyrazol-1-yl]propane-1,2-diol;

4-[4-amino-5-(2,3,4-trihydroxy-butyl-amino)pyra-zol-1-yl]-butane-1,2,3-triol;

4-(4-amino-5-isopro-pylamino-pyrazol-1-yl)butane-1,2,3-triol, and the physiologically acceptable salts thereof.

19. The process according to claim 18, wherein the at least one diaminopyrazole compound is chosen from:

3-(4-amino-5-ethylaminopyrazol-1-yl)propane-1,2-diol and the physiologically acceptable acid salts thereof.

20. The process according to claim 17, wherein said composition is applied to the keratin fibers in the presence of at least one oxidation catalyst.

21. The process according to claim 17, wherein said color is revealed on contact with atmospheric oxygen.

22. The process according to claim 17, wherein said color is revealed at acidic, neutral or alkaline pH with the aid of at least one oxidizing agent, which is added to the dye composition at the time of use, or which is present in an oxidizing composition applied simultaneously or sequentially in a separate manner.

23. The process according to claim 17, wherein said at least one oxidizing agent is chosen from hydrogen peroxide, urea peroxide, alkali metal bromates, and persalts.

24. The process according to claim 23, wherein said persalts are chosen from perborates and persulfates.

25. The process according to claim 17, wherein the composition for oxidation dyeing further comprises at least one coupler chosen from 5-N-([β]-hydroxyethyl)amino-2-methyl-phenol, 6-chloro-2-methyl-5-aminophenol, 3-aminophenol, 1,3-dihydroxy-2-methylbenzene, 4-chloro-1,3-dihydroxybenzene, 2,4-diamino-1-([β]-hydroxy-ethyloxy) benzene, 2-amino-4-([β]-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-[β]-hydroxyethylamino-3,4-methylenedioxybenzene,[α]-naphthol, 2-methyl-1-naphthol, 6-hydroxyindole, 4-hydroxyindote, 4-hydroxy-N-methylindole, 2-amino-3-hydroxypyridme, 6-hydroxybenzomorpholine, 3,5-diamino-2,6-dimethoxypyridine, 1-N-([β]-hydroxyethyl)amino-3,4-methylene-dioxybenzene and 2,6-bis([β]-hydroxyethylamino)toluene, and the addition salts thereof.

26. The process according to claim 17, wherein said keratin fibers are human hair.

27. A multi-compartment device comprising:

a first compartment containing a composition for the oxidation dyeing of keratin fibers, comprising, in a medium suitable for dying, at least one oxidation base, chosen from diaminopyrazole compounds chosen from:

| Structure | Name |
|---|---|
| (structure) | 4-(4-amino-2-isopropyl-2H-pyrazol-3-ylamino)-3-methylbutan-1-ol |

-continued

| Structure | Name |
|---|---|
| 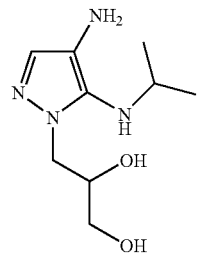 | 3-(4-amino-5-isopropylamino-pyrazol-1-yl)propane-1,2-diol |
| 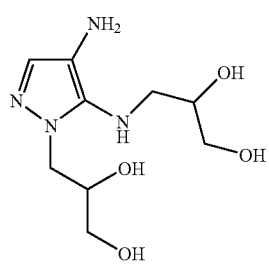 | 3-[4-amino-5-(2,3-dihydroxypropylamino)-pyrazol-1-yl]propane-1,2-diol |
| 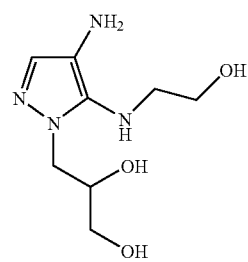 | 3-[4-amino-5-(2-hydroxyethylamino)pyrazol-1-yl]propane-1,2-diol |
| 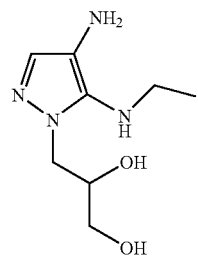 | 3-(4-amino-5-ethylamino-pyrazol-1-yl)propane-1,2-diol |
| 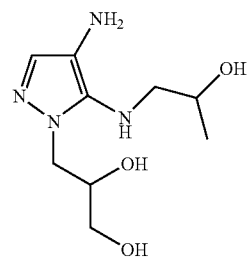 | 3-[4-amino-5-(2-hydroxypropylamino)-pyrazol-1-yl]propane-1,2-diol |

-continued

| Structure | Name |
|---|---|
| 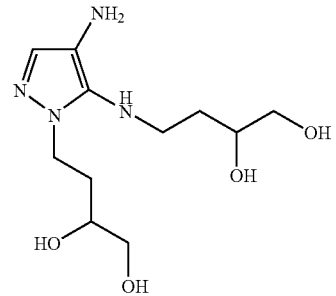 | 4-[4-amino-5-(3,4-dihydroxybutylamino)-pyrazol-1-yl]butane-1,2-diol |
| 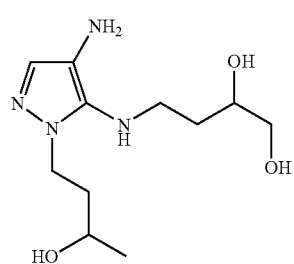 | 4-[4-amino-2-(3-hydroxybutyl)-2H-pyrazol-3-ylamino]-butane-1,2-diol |
| 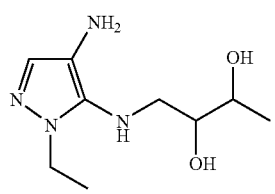 | 1-(4-amino-2-ethyl-2H-pyrazol-3-ylamino)-butane-2,3-diol |
| 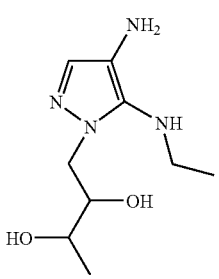 | 1-(4-amino-5-ethyl-aminopyrazol-1-yl)butane-2,3-diol |
| 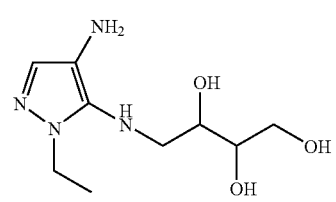 | 4-(4-amino-2-ethyl-2H-pyrazol-3-ylamino)-butane-1,2,3-triol |
| 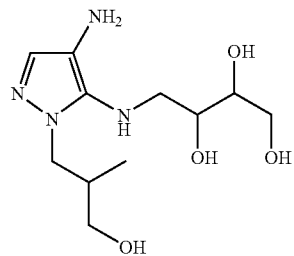 | 4-[4-amino-2-(3-hydroxy-2-methylpropyl)-2H-pyrazol-3-ylamino]-butane-1,2,3-triol |

-continued

| Structure | Name |
|---|---|
| 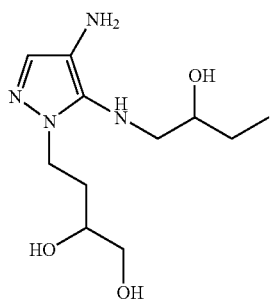 | 4-[4-amino-5-(2-hydroxybutyl-amino)pyrazol-1-yl]butane-1,2-diol |
| 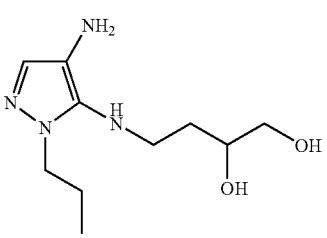 | 4-(4-amino-2-propyl-2H-pyrazol-3-ylamino)-butane-1,2-diol |
| 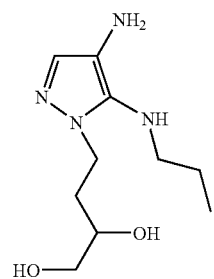 | 4-(4-amino-5-propyl-aminopyrazol-1-yl)butane-1,2-diol |
| 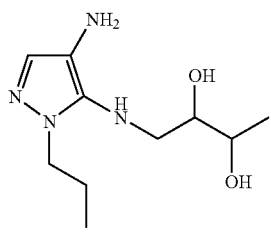 | 1-(4-amino-2-propyl-2H-pyrazol-3-ylamino)-butane-2,3-diol |
| 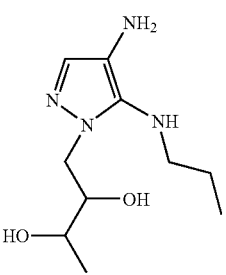 | 4-(4-amino-5-propyl-aminopyrazol-1-yl)butane-1,2-diol |

-continued

| Structure | Name |
|---|---|
| 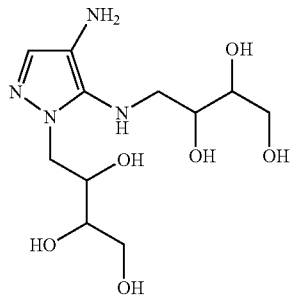 | 4-[4-amino-5-(2,3,4-trihydroxybutyl-amino)pyrazol-1-yl]butane-1,2,3-triol |
| 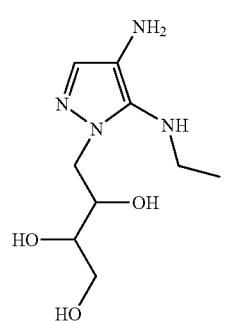 | 4-(4-amino-5-ethyl-aminopyrazol-1-yl)butane-1,2,3-triol |
| 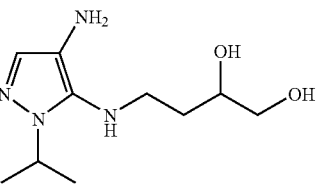 | 4-(4-amino-2-isopropyl-2H-pyrazol-3-ylamino)-butane-1,2-diol |
| 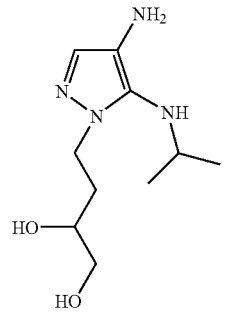 | 4-(4-amino-5-isopropylamino-pyrazol-1-yl)butane-1,2-diol |
| 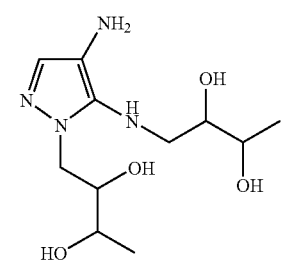 | 1-[4-amino-5-(2,3-dihydroxybutylamino)-pyrazol-1-yl]butane-2,3-diol |

| Structure | Name |
|---|---|
| 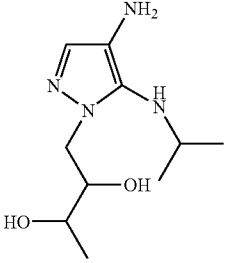 | 4-(4-amino-5-isopropylamino-pyrazol-1-yl)butane-1,2-diol |
| 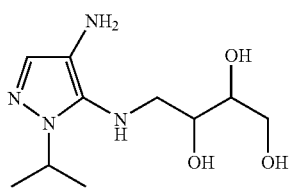 | 4-(4-amino-2-isopropyl-2H-pyrazol-3-ylamino)-butane-1,2,3-triol |
| 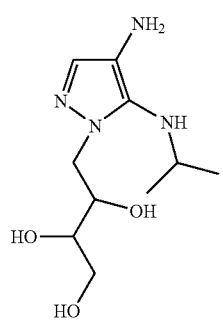 | 4-(4-amino-5-isopropylamino-pyrazol-1-yl)butane-1,2,3-triol |
| 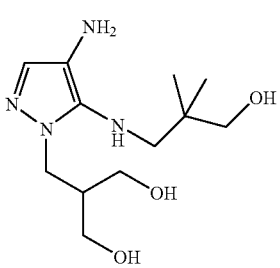 | 2-[4-amino-5-(3-hydroxy-2,2-dimethylpropyl-amino)pyrazol-1-ylmethyl]-propane-1,3-diol |
| 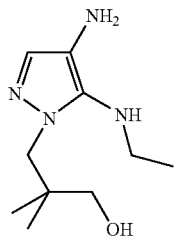 | 3-(4-amino-5-ethyl-aminopyrazol-1-yl)-2,2-dimethylpropan-1-ol |
| 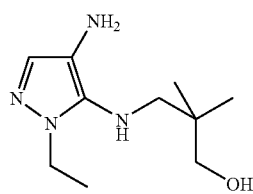 | 3-(4-amino-2-ethyl-2H-pyrazol-3-ylamino)-2,2-dimethyl-propan-1-ol |

| Structure | Name |
|---|---|
| 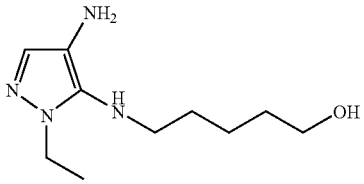 | 5-(4-amino-2-ethyl-2H-pyrazol-3-ylamino)-pentan-1-ol |
| 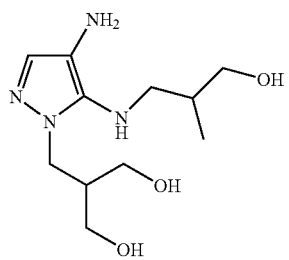 | 2-[4-amino-5-(3-hydroxy-2-methylpropylamino)-pyrazol-1-ylmethyl]-propane-1,3-diol |
| 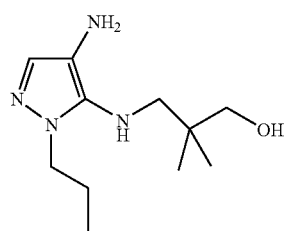 | 3-(4-amino-2-propyl-2H-pyrazol-3-ylamino)-2,2-dimethyl-propan-1-ol |
| 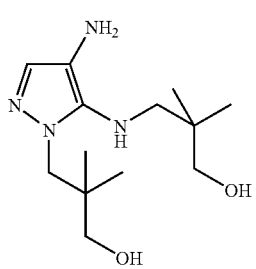 | 3-[4-amino-5-(3-hydroxy-2,2-dimethylpropyl-amino)pyrazol-1-yl]-2,2-dimethylpropan-1-ol |
| 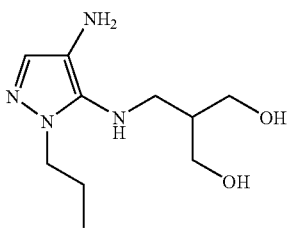 | 2-[(4-amino-2-propyl-2H-pyrazol-3-ylamino)-methyl]-propane-1,3-diol |
| 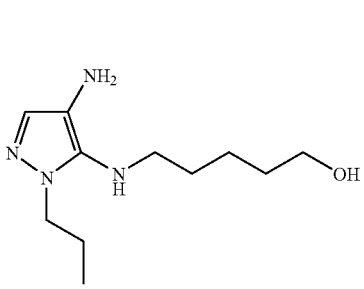 | 5-(4-amino-2-propyl-2H-pyrazol-3-ylamino)-pentan-1-ol |

-continued

| Structure | Name |
|---|---|
| 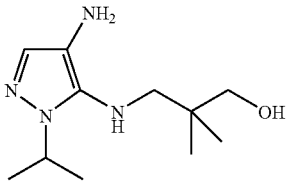 | 3-(4-amino-2-isopropyl-2H-pyrazol-3-ylamino)-2,2-dimethyl-propan-1-ol |
| 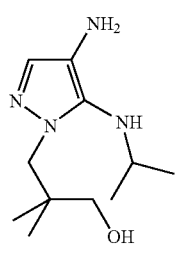 | 3-(4-amino-5-isopropylamino-pyrazol-1-yl)-2,2-dimethyl-propan-1-ol |
| 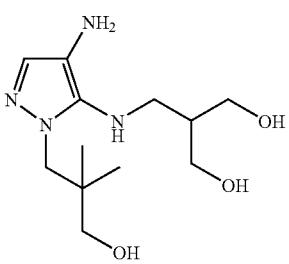 | 2-{[4-amino-2-(3-hydroxy-2,2-dimethylpropyl)-2H-pyrazol-3-ylamino]methyl}proane-1,3-diol |
| 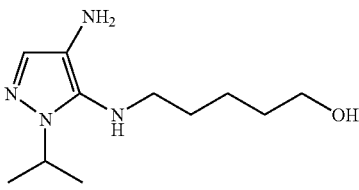 | 5-(4-amino-2-isopropyl-2H-pyrazol-3-ylamino)-pentan-1-ol |
| 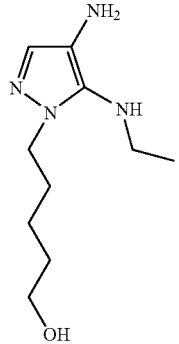 | 5-(4-amino-5-ethyl-aminopyrazol-1-yl)pentan-1-ol |
| 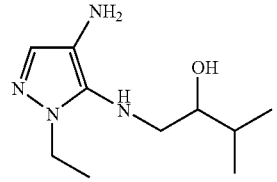 | 1-(4-amino-2-ethyl-2H-pyrazol-3-ylamino)-3-methylbutan-2-ol |

-continued

| Structure | Name |
|---|---|
| 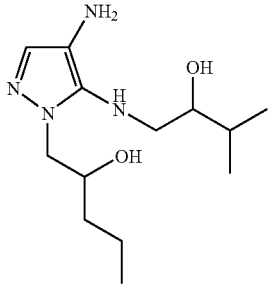 | 1-[4-amino-5-(2-hydroxy-3-methylbutylamino)-pyrazol-1-yl]pentan-2-ol |
| 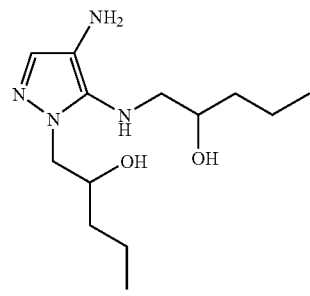 | 1-[4-amino-5-(2-hydroxypentylamino)-pyrazol-1-yl]pentan-2-ol |
| 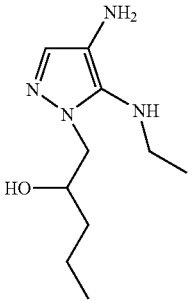 | 1-(4-amino-5-ethylamino-pyrazol-1-yl)pentan-2-ol |
| 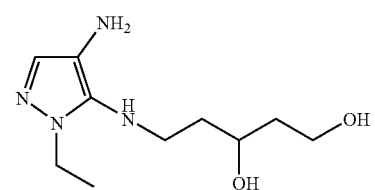 | 5-(4-amino-2-ethyl-2H-pyrazol-3-ylamino)-pentane-1,3-diol |
| 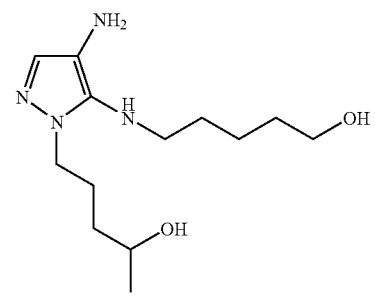 | 5-[4-amino-2-(4-hydroxypentyl)-2H-pyrazol-3-ylamino]-pentan-1-ol |

-continued

| Structure | Name |
|---|---|
| 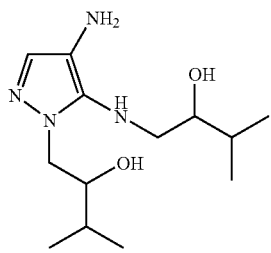 | 1-[4-amino-5-(2-hydroxy-3-methylbutylamino)-pyrazol-1-yl]-3-methylbutan-2-ol |
| 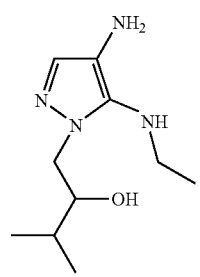 | 1-(4-amino-5-ethylamino-pyrazol-1-yl)-3-methylbutan-2-ol |
| 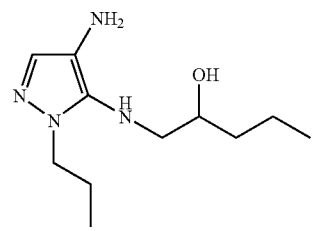 | 1-(4-amino-2-propyl-2H-pyrazol-3-ylamino)-pentan-2-ol |
| 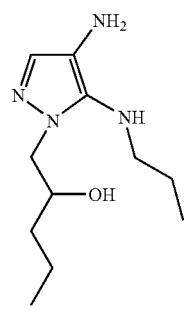 | 1-(4-amino-5-propylamino-pyrazol-1-yl)pentan-2-ol |
| 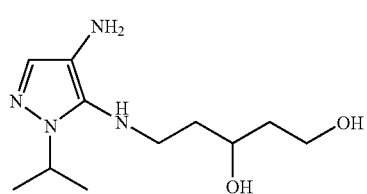 | 5-(4-amino-2-isopropyl-2H-pyrazol-3-ylamino)-pentane-1,3-diol |

-continued

| Structure | Name |
|---|---|
| 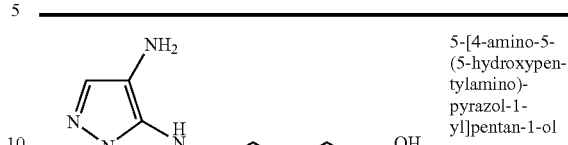 | 5-[4-amino-5-(5-hydroxypentylamino)-pyrazol-1-yl]pentan-1-ol |
| 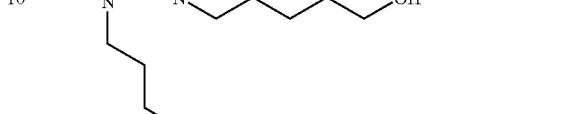 | 1-(4-amino-2-isopropyl-2H-pyrazol-3-ylamino)-3-methylbutan-2-ol |
| 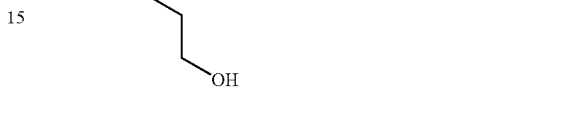 | 1-(4-amino-5-propylamino-pyrazol-1-yl)-3-methylbutan-2-ol |
| 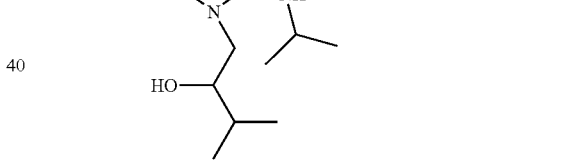 | 1-(4-amino-2-isopropyl-2H-pyrazol-3-ylamino)-pentan-2-ol |
| 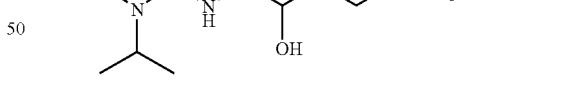 | 5-[4-amino-5-(3-hydroxypentylamino)-pyrazol-1-yl]-pentane-1,2-diol |

-continued

| Structure | Name |
|---|---|
| 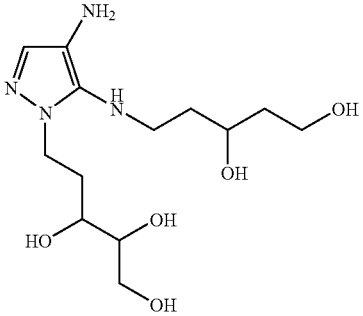 | 5-[4-amino-5-(3,5-di-hydroxypen-tylamino)-pyrazol-1-yl]pentane-1,2,3-triol |
| 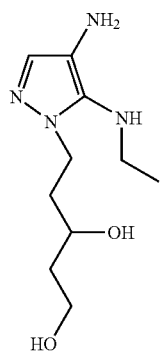 | 5-(4-amino-5-ethyl-aminopyrazol-1-yl)pentane-1,3-diol |
| 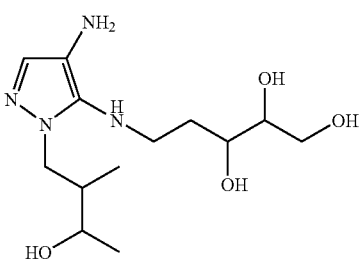 | 5-[4-amino-2-(3-hydroxy-2-methylbutyl)-2H-pyrazol-3-ylamino]-pentane-1,2,3-triol |
| 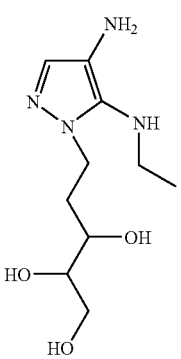 | 5-(4-amino-5-ethylamino-pyrazol-1-yl)pentane-1,2,3-triol |
| 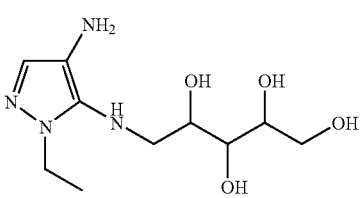 | 5-(4-amino-2-ethyl-2H-pyrazol-3-ylamino)-pentane-1,2,3,4-tetraol |

-continued

| Structure | Name |
|---|---|
| 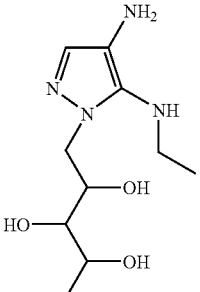 | 5-(4-amino-5-ethylamino-pyrazol-1-yl)pentane-1,2,3,4-tetraol |
| 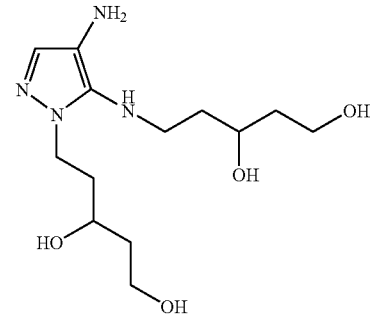 | 5-[4-amino-5-(3,5-di-hydroxypen-tylamino)-pyrazol-1-yl]pentane-1,3-diol |
| 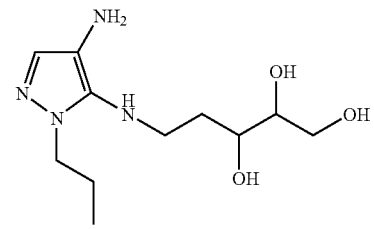 | 5-(4-amino-2-propyl-2H-pyrazol-3-ylamino)-pentane-1,2,3-triol |
| 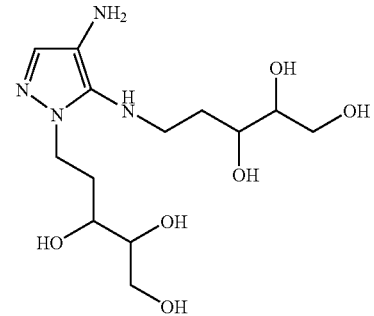 | 5-[4-amino-5-(3,4,5-trihydroxy-pentylamino)-pyrazol-1-yl]pentane-1,2,3-triol |
| 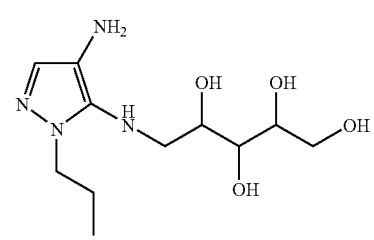 | 5-(4-amino-2-propyl-2H-pyrazol-3-ylamino)-pentane-1,2,3,4-tetraol |

-continued

| Structure | Name |
|---|---|
| 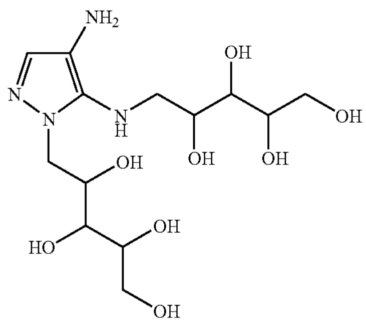 | 5-[4-amino-5-(2,3,4,5-tetra-hydroxypentyl-amino)pyrazol-1-yl]pentane-1,2,3,4-tetraol |
| 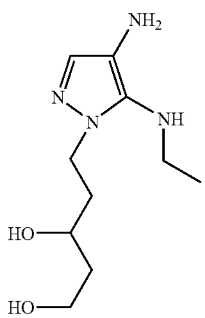 | 5-(4-amino-5-ethylamino-pyrazol-1-yl)pentane-1,3-diol |
| 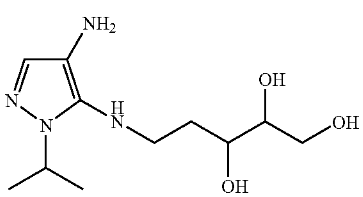 | 5-(4-amino-2-isopropyl-2H-pyrazol-3-ylamino)-pentane-1,2,3-triol |

-continued

| Structure | Name |
|---|---|
| 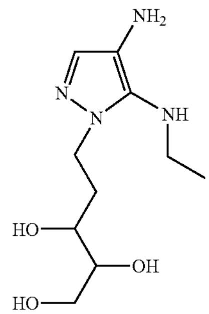 | 5-(4-amino-5-ethylamino-pyrazol-1-yl)pentane-1,2,3-triol |
| 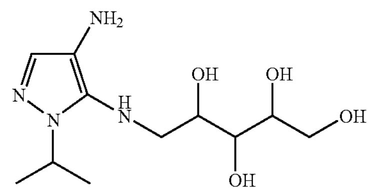 | 5-(4-amino-2-isopropyl-2H-pyrazol-3-ylamino)-pentane-1,2,3,4-tetraol |
| | 5-[4-amino-2-(2-hydroxymeth-ylbutyl)-2H-pyrazol-3-ylamino]-pentane-1,2,3,4-tetraol | and the physiologically acceptable salts,
and a second compartment containing an oxidizing composition.

* * * * *

UNITED STATES PATENT AND TRADEMARK OFFICE
CERTIFICATE OF CORRECTION

PATENT NO. : 7,300,469 B2
APPLICATION NO. : 10/468303
DATED : November 27, 2007
INVENTOR(S) : Fessman et al.

Page 1 of 2

It is certified that error appears in the above-identified patent and that said Letters Patent is hereby corrected as shown below:

On the title page, item (73), "L'Oreal, SA," should read --L'Oreal SA,--.

On the title page, item (57), line 3, "$C_3$ $C_5$" should read --$C_3$-$C_5$--.

In claim 1, column 44, lines 35-41, "2-{[4-amino-2-(3-hydroxy-2,2-dimethylpropyl)-2H-pyrazol-3-ylamino]-methyl}proane-1,3-diol" should read --2-{[4-amino-2-(3-hydroxy-2,2-dimethylpropyl)-2H-pyrazol-3-ylamino]-methyl}propane-1,3-diol--.

In claim 2, column 51, lines 27-28, "3-(4-amino-5-isopro-pylamino-pyrazol-1-yl)prepane-1,2-diol;" should read --3-(4-amino-5-isopro-pylamino-pyrazol-1-yl)propane-1,2-diol;--.

In claim 2, column 51, lines 29-30, "3-[4-amino-5-(2,3-di-hydroxypro-pylamino)-pyrazol-1-yl]prepane-1,2-diol;" should read --3-[4-amino-5-(2,3-di-hydroxypro-pylamino)-pyrazol-1-yl]propane-1,2-diol;--.

In claim 2, column 51, lines 33-34, "3[4-amino5-(2-hy-droxyethyl-amino)-pyrazol-1-yl]-propane-1,2-diol;" should read --3-[4-amino-5-(2-hy-droxyethyl-amino)-pyrazol-1-yl]-propane-1,2-diol;--.

In claim 2, column 51, lines 45-46, "4-(4-amino-5-(isopro-pylamino-pyrazol-1-yl )butane-1,2,3-triol," should read --4-(4-amino-5-(isopro-pylamino-pyrazol-1-yl)butane-1,2,3-triol,--.

In claim 10, column 52, line 10, "present an" should read --present in an--.

In claim 12, column 52, line 18, "mono-or" should read --mono- or--.

In claim 13, column 52, line 26, "4-chloro-1,3-dihyd roxybenzene," should read --4-chloro-1,3-dihydroxybenzene,--.

In claim 13, column 52, lines 29-30, "3-ureido-1-di-methylaminobenzene,sesamol," should read --3-ureido-1-di-methylaminobenzene, sesamol,--.

In claim 13, column 52, lines 30-32, "1-[beta]-hydroxyethylamino-3,4-methylenedioxybenzene,[α]-naphthol," should read --1-[beta]-hydroxyethylamino-3,4-methylenedioxybenzene, [α]-naphthol,--.

In claim 13, column 52, lines 33-34, "2-amino-3-hydroxypyridme," should read --2-amino-3-hydroxypyridine,--.

UNITED STATES PATENT AND TRADEMARK OFFICE
CERTIFICATE OF CORRECTION

PATENT NO. : 7,300,469 B2  
APPLICATION NO. : 10/468303  
DATED : November 27, 2007  
INVENTOR(S) : Fessman et al.

Page 2 of 2

It is certified that error appears in the above-identified patent and that said Letters Patent is hereby corrected as shown below:

In claim 13, column 52, lines 35-36, "1-N-([β]-hydroyethyl)amino-3,4-methylene-d ioxybenzene" should read --1-N-([β]-hydroyethyl)amino-3,4-methylene-dioxybenzene--.

In claim 17, column 60, lines 5-11, "2-{[4-amino-2-(3-hydroxy-2,2-dimethylpropyl)-2H-pyrazol-3-ylamino]-methyl}proane-1,3-diol" should read --2-{[4-amino-2-(3-hydroxy-2,2-dimethylpropyl)-2H-pyrazol-3-ylamino]-methyl}propane-1,3-diol--.

In claim 18, column 65, lines 62-63, "3-[4-amino5-(2-hy-droxyethyl-amino)-pyrazol-1-yl]-propane-1,2-diol;" should read --3-[4-amino-5-(2-hy-droxyethyl-amino)-pyrazol-1-yl]-propane-1,2-diol;--.

In claim 25, column 66, lines 39-40, "1-[β]-hydroxyethylamino-3,4-methylenedioxybenzene,[α]-naphthol," should read --1-[β]-hydroxyethylamino-3,4-methylenedioxybenzene, [α]-naphthol,--.

In claim 25, column 66, line 41, "4-hydroxyindote," should read --4-hydroxyindole,--.

In claim 25, column 66, line 42, "2-amino-3-hydroxypyridme," should read --2-amino-3-hydroxypyridine,--.

In claim 27, column 73, lines 25-31, "2-{[4-amino-2-(3-hydroxy-2,2-dimethylpropyl)-2H-pyrazol-3-ylamino]-methyl}proane-1,3-diol" should read --2-{[4-amino-2-(3-hydroxy-2,2-dimethylpropyl)-2H-pyrazol-3-ylamino]-methyl}propane-1,3-diol--.

Signed and Sealed this

Fifteenth Day of September, 2009

David J. Kappos  
*Director of the United States Patent and Trademark Office*